US010698065B2

(12) United States Patent
Novikov et al.

(10) Patent No.: US 10,698,065 B2
(45) Date of Patent: Jun. 30, 2020

(54) SYSTEM, METHOD AND COMPUTER ACCESSIBLE MEDIUM FOR NOISE ESTIMATION, NOISE REMOVAL AND GIBBS RINGING REMOVAL

(71) Applicants: New York University, New York, NY (US); University of Antwerp, Antwerp (BE)

(72) Inventors: Dmitry Novikov, New York, NY (US); Jelle Veraart, Brooklyn, NY (US); Els Fieremans, New York, NY (US)

(73) Assignees: New York University, New York, NY (US); University of Antwerp, Antwerp (BE)

( * ) Notice: Subject to any disclaimer, the term of this patent is extended or adjusted under 35 U.S.C. 154(b) by 75 days.

(21) Appl. No.: 15/574,467

(22) PCT Filed: May 16, 2016

(86) PCT No.: PCT/US2016/032761
§ 371 (c)(1),
(2) Date: Nov. 15, 2017

(87) PCT Pub. No.: WO2016/187148
PCT Pub. Date: Nov. 24, 2016

(65) Prior Publication Data
US 2018/0120404 A1    May 3, 2018

Related U.S. Application Data

(60) Provisional application No. 62/162,164, filed on May 15, 2015, provisional application No. 62/317,061, filed on Apr. 1, 2016.

(51) Int. Cl.
*A61B 5/055*  (2006.01)
*G01R 33/563* (2006.01)
(Continued)

(52) U.S. Cl.
CPC ...... *G01R 33/56545* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 5,285,157 A    2/1994  Zur
8,030,924 B2  10/2011  Bito et al.
(Continued)

OTHER PUBLICATIONS

Ahmed, Adeel et al., "Noise Variance Estimation for Spectrum Sensing in Cognitive Radio Networks," AASRI Procedia, vol. 9, pp. 37-43, 2014.
(Continued)

*Primary Examiner* — Idowu O Osifade
(74) *Attorney, Agent, or Firm* — Hunton Andrews Kurth LLP

(57) ABSTRACT

An exemplary system, method and computer-accessible medium for removing noise and Gibbs ringing from a magnetic resonance ("MR") image(s), can be provided, which can include, for example, receiving information related to the MR image(s), receiving information related to the MR image(s), and removing the Gibbs ringing from the information by extrapolating data in a k-space from the MR image(s) beyond an edge(s) of a measured portion of the k-space. The data can be extrapolated by formatting the data as a regularized minimization problem(s). A first weighted term of the regularized minimization problem(s) can preserve a fidelity of the extrapolated data, and a second weighted term of the regularized minimization problem(s) can be a penalty term that can be based a norm(s) of the MR image(s), which can be presumed to be sparse.

15 Claims, 24 Drawing Sheets

(51) Int. Cl.
| | |
|---|---|
| A61B 5/00 | (2006.01) |
| G01R 33/565 | (2006.01) |
| G06K 9/40 | (2006.01) |
| G06K 9/62 | (2006.01) |
| G06T 7/00 | (2017.01) |

(52) U.S. Cl.
CPC ...... *A61B 5/7203* (2013.01); *G01R 33/56341* (2013.01); *G06K 9/40* (2013.01); *G06K 9/6247* (2013.01); *G06T 7/0016* (2013.01); *A61B 2576/026* (2013.01); *G06K 2209/051* (2013.01); *G06T 2207/10088* (2013.01)

(56) References Cited

U.S. PATENT DOCUMENTS

| | | | |
|---|---|---|---|
| 2007/0016837 A1* | 1/2007 | Candes | H03M 13/03 714/746 |
| 2009/0093709 A1 | 4/2009 | Patel et al. | |
| 2010/0260402 A1 | 10/2010 | Axelsson et al. | |
| 2012/0269414 A1 | 10/2012 | Zha et al. | |
| 2013/0096425 A1 | 4/2013 | Untela et al. | |
| 2014/0212015 A1 | 7/2014 | Ding et al. | |
| 2017/0046557 A1* | 2/2017 | Laleg-Kirati | G06T 5/002 |

OTHER PUBLICATIONS

Basser, Peter J. et al., "MR Diffusion Tensor Spectroscopy and Imaging," Biophysical Journal, vol. 66, pp 259-276, Jan. 1994.
Basser, Peter J. et al., "Statistical Artifacts in Diffusion Tensor MRI (DT-MRI) Cause by Background Noise," Magnetic Resonance in Medicine, vol. 44, pp. 41-50, 2000.
Block, Kai Tobias et al., "Suppression of MRI Truncation Artifacts Using Total Variation Constrained Data Extrapolation, " International Journal of Biomedical Imaging, vol. 2008, Article ID 184123, pp. 1-9, 2008.
Bredies, Kristian et al., "Spatially Dependent Regularization Parameter Selection in Total Generalized Variation Models for Image Restoration," International journal of Computer Mathematics, vol. 90, No. 1 , pp. 109-123, 2013.
Buades, Antoni et al., "A Non-Local Algorithm for Image Denoising," IEEE Computer Society Conference on IEEE, vol. 2, pp. 60-65, 2005.
Chambolle, Antonin et al., "A First-Order Primal-Dual Algorithm for Convex Problems with Applications to Imaging," Math Imag. and Vision, vol. 40, No. 120, pp. 1-49, Jun. 9, 2010.
Chang, Lin-Ching et al., "RESTORE: Robust Estimation of Tensors by Outlier Rejection," Magnetic Resonance in Medicine, vol. 53, pp. 1088-1095, 2005.
Coupe, Pierrick et al., "Fast Non Local Means Denoising for 3D MR Images," Medical Image Computing and Computer-Assisted Intervention-MICCAI 2006, Springer, pp. 33-40, 2006.
Coupe, Pierrick et al., "Robust Rician Noise Estimation for MR Images," Medical Image Analysis, vol. 14, pp. 483-493, 2010.
Deledalle, Charles-Alban et al., "Image Denoising with Patch-Based PCA: Local Versus Global," The 22nd British Machine Vision Conference, Univeristy of Dundee, Aug. 29,-Sep. 2, 2011, pp. 1-32, Aug. 31, 2011.
Ding, Yu et al., "A Method to Assess Spatially Variant Noise in Dynamic MR Image Series," Magnetic Resonance in Medicine, vol. 63, pp. 782-789, 2010.
"Breakthroughs in Statistics, vol. II, Methodology and Distribution," Springer Series in Statistics, Springer, pp. 1-613, 1992.
Aja-Fernandez, Santiago et al., "Statistical Noise Analysis in GRAPPA Using a Parametrized Noncentral Chi Approximation Model," Magn. Reson. Med., vol. 65, No. 4, pp. 1195-1206, Apr. 2011.
Fieremans, Els et al., "White Matter Characterization with Diffusional Kurtosis Imaging," Neuroimage, vol. 58, No. 1, pp. 177-188, Sep. 1, 2011.
Foi, Alessandro, "Noise Estimation and Removal in MR Imaging: The Variance-Stabilization Approach," Biomedical Imaging: From Nano to Macro, 2011 IEEE International Symposium on IEEE, pp. 1809-1814, 2011.
Glasser, Matthew F. et al., "The Minimal Preprocessing Pipelines for the Human Connectome Project," NeuroImage, vol. 80, pp. 105-124, 2013.
Gudbjartsson, Hakon et al., "The Rician Distribution of Noisy MRI Data," Magn. Reson. Med., vol. 34, No. 6, pp. 910-914, Dec. 1995.
Hotelling, Harold, "Analysis of a Complex of Statistical Variables into Principal Components," Journal of Educational Psychology, vol. 24, pp. 417-441, 1933.
Hunt, B.R., "The Application of Constrained Least Squares Estimation to Image Restoration by Digital Computer," IEEE Transactions on Computers, vol. C-22, No. 9, pp. 805-812, Sep. 1973.
Jahani, Jeiran et al., "Random Matrix Theory-Based Noise Reduction for Dynamic Imaging: Application to DCE-MRI," Proceedings 21th Scientific Meeting, International Society for Magnetic Resonance in Medicine, Salt Lake City, USA, vol. 21, p. 3073, 2013.
Jelescu, Iieana O. et al., "Degeneracy in Model Parameter Estimation for Multi-Compartmental Diffusion in Neural Tissue," NMR Biomed., vol. 29, pp. 33-47, 2016.
Jeurissen, Ben et al., "Investigating the Prevalence of Complex Fiber Configurations in White Matter Tissue with Diffusion Magnetic Resonance Imaging," Human Brain Mapping, vol. 34, pp. 2747-2766, 2013.
Jeurissen, Ben et al., "Probabilistic Fiber Tracking Using the Residual Bootstrap with Constrained Spherical Deconvolution," Human Brain Mapping, vol. 32, pp. 461-479, 2011.
Johnstone, Iain M., "High Dimensional Statistical Inference and Random Matrices," pp. 1-28, Nov. 19, 2006.
Jones, D.K. et al., "Optimal Strategies for Measuring Diffusion in Anisotropic Systems by Magnetic Resonance Imaging," Magnetic Resonance in Medicine, vol. 42, pp. 515-525, 1999 (Has a Dup).
Jones, Derek K., "Determining and Visualizing Uncertainty in Estimates of Fiber Orientation From Diffusion Tensor MRI," Magnetic Resonance in Medicine, vol. 49, pp. 7-12, 2003.
Jones, Derek K. et al., ""Squashing Peanuts and Smashing Pumpkins": how Noise Distorts Diffusion-Weighted MR Data," Magnetic Resonance in Medicine, vol. 52, pp. 979-993, 2004.
Jones, Derek K. et al., "Presision and Accuracy in Diffusion Tensor Magnetic Resonance Imaging," Topics in Magnetic Resonance Imaging, vol. 21, pp. 87-99, 2010.
Keil, Boris et al., "A 64-Channel 3T Array Coil for Accelerated Brain MRI," Magnetic Resonance in Medicine, vol. 70, pp. 248-258, 2013.
Kellner, Elias et al., "Gibbs-Ringing Artifact Removal Based on Local Subvoxel-Shifts," Magnetic Resonance in Medicine, vol. 76, pp. 1574-1581, 2016.
Knoll, Florian et al., "Second Order Total Generalized Variation (TGV) for MRI," Magnetic Resonance in Medicine, vol. 65, pp. 480-491, 2011.
Koay, Cheng Guan et al., "Analytically Exact Correction Scheme for Signal Extraction from Noisy Magnitude MR Signals," Journal of Magnetic Resonance, vol. 179, pp. 317-322, 2006.
Laloux, Laurent et al., "Noise Dressing of Financial Correlation Matrices," vol. 83, No. 7, Physical Review Letters, pp. 1467-1470, Aug. 16, 1999.
Manjon, Jose V. et al., "MRI Noise Estimation and Denoising using Non-Local PCA," Medical Image Analysis, vol. 22, pp. 35-47, 2015.
Manjon, Jose V. et al., "Diffusion Weighted Image Denoising Using Overcomplete Local PCA," PLOS One, vol. 8, Issue No. 9, pp. 1-12, Sep. 2013.
Manjon, Jose V. et al., "Adaptive Non-Local Means Denoising of MR Images With Spatially Varying Noise Levels," Journal of Magnetic Resonance Imaging, vol. 31, pp. 192-203, 2010.
Manjon, Jose V. et al., "MRI Denoising Using Non-Local Means," Medical Image Analysis, vol. 12, pp. 514-523, 2008.
Marcenko, V.A. et al., "distribution of Eigenvalues for Some Sets of Random Matrices," Math. USSR-Sbornil, vol. 1, No 4, pp. 1-28, 1967.

(56) References Cited

OTHER PUBLICATIONS

"Reviewers—An Acknowledgement," Medical Image Analysis, vol. 44, pp. iii-iv, 2018.
Nyquist, H., "Thermal Agitation of Electric Charge in Conductors," Physical Review, vol. 32, pp. 110-113, Jul. 1928.
Orchard, Jeff et al., "Efficient Nonlocal-Means Denoising using the SVD," ICIP 2008 15th IEEE International Conference on IEEE, pp. 1732-1735, 2008.
Perrone, Daniele et al., "The Effect of Gibbs Ringing Artifacts on Measures Derived from Diffusion MRI," NeuroImage, vol. 120, pp. 441-455, 2015 [Has Dup].
Poot, Dirk H. J. et al., "Optimal Experimental Design for Diffusion Kurtosis Imaging," IEEE Transactions on Medical Imaging, vol. 29, No. 3, pp. 819-829, Mar. 2010.
Rajan, Jeny et al., "Maximum Likelihood Estimation-based Denoising of Magnetic Resonance Images Using Restricted Local Neighborhoods," Phys. Med. Biol., vol. 56, pp. 5221-5234, 2011.
Rajan, Jeny et al., "Nonlocal Maximum Likelihood Estimation Method for Denoising Multiple-Coil Magnetic Resonance Images," Magnetic Resonance Imaging, vol. 30, pp. 1512-1518, 2012.
Rudin, Leonid I. et al., "Nonlinear Total Variation based Noise Removal Algorithms," Physica D, vol. 60, pp. 259-268, 1992.
Sengupta, A.M. et al., "Distributions of Singular Values for Some Random Matricies," Physical Review E, vol. 60, No. 3, pp. 3389-3392, Sep. 1999.
Setsompop, K. et al., "Pushing the Limits of in vivo Diffusion MRI for the Human Connectome Project," NeuroImage, vol. 80, pp. 220-233, 2013.
Smith, Stephen M. et al., "Advances in Functional and Structural MR Image Analysis and Implementation as FSL," NeuroImage, vol. 23, pp. S208-S219, 2004.
Knoll, Florian et al., "Second Order Total Generalized Variation (TGV) for MRI," Graz University of Technology, pp. 1-25, 2010.
International Search Report and Written Opinion dated Aug. 18, 2016 for International Application No. PCT/US2016/032761.
Maximov, Ivan I. et al., "Spatially Variable Rician Noise in Magnetic Resonance Imaging," Medical Image Analysis, vol. 16, pp. 536-548, 2012.
Bredies, Kristian et al., "Total Generalized Variation," Siam J. Imaging Sciences, vol. 3, No. 3, pp. 492-526, 2010.
Jones, Derek K., "MRI Theory, Methods, and Applications," Oxford Univeristy Press, pp. 1-770, 2010.
Sotiropoulos, Stamatios N. et al., "Advances in Diffusion MRI Acquisition and Processing in the Human Connectome Project," NeuroImage, vol. 80, pp. 125-143, 2013.
Tax, Chantal M.W. et al., "Recursive Calibration of the Fiber Response Function for Spherical Deconvolution of Diffusion MRI Data," NeuroImage, vol. 86, pp. 67-80, 2014.
Tournier, J-Donald et al., "Robust Determination of the Fibre Orientation Distribution in Diffusion MRI: Non-negativity Constrainted Super-Resolved Spherical Deconvolution," NeuroImage, vol. 35, pp. 1459-1472, 2007.
Veraart, Jelle et al., "Weighted Linear least Squares Estimation of Diffusion MRI Parameters: Strengths, Limitations, and Pitfalls," NeuroImage, vol. 81, pp. 335-346, 2013.
Veraart, Jelle et al., "Comprehensive Framework for Accurate Diffusion MRI Parameter Estimation," Magnetic Resonance in Medicine, vol. 70, pp. 972-984, 2013.
Veraart, Jelle et al., "More Accurate Estimation of Diffusion Tensor Parameters Using Diffusion Kurtosis Imaging," Magnetic Resonance in Medicine, vol. 65, pp. 138-145, 2011.
Veraart, Jelle et al., "Constrained Maximum Likelihood Estimation of the Diffusion Kurtosis Tensor Using a Rician Noise Model," Magnetic Resonance in Medicine, vol. 66, pp. 678-686, 2011.
Veraart, Jelle et al., "Diffusion MRI Noise Mapping Using Random Matrix Theory," Magnetic Resonance in Medicine, vol. 76, pp. 1582-1593, 2016.
Veraart, Jelle et al., "Gibbs ringing in Diffusion MRI," Magn. Reson. Med., vol. 76, No. 1, pp. 301-314, Jul. 2016.
Marchenko, V. A. et al., "Distribution of Eigenvalues for some Sets of Random Matrices," Math-Net.Ru, All Russian Mathematical Portal, vol. 72, No. 4, pp. 507-536, 1967.

\* cited by examiner

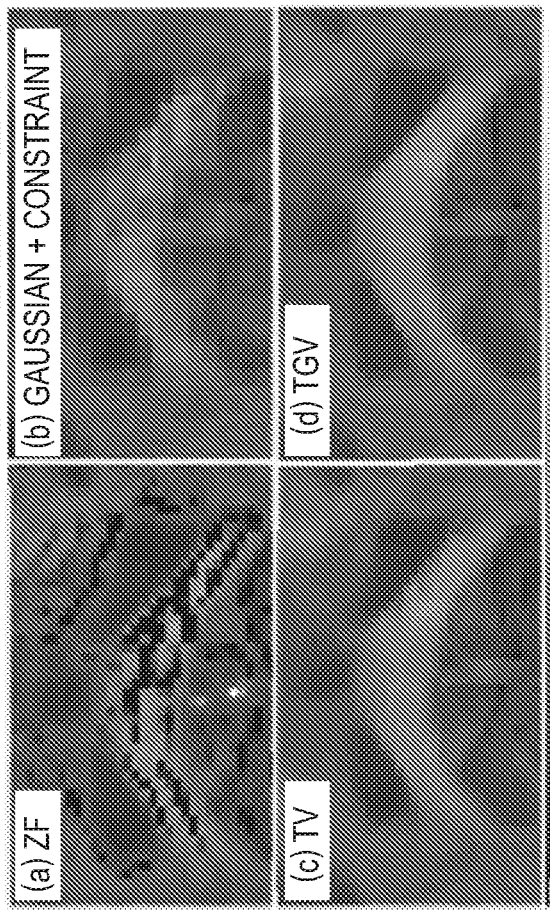
FIG. 4A  FIG. 4B
FIG. 4C  FIG. 4D
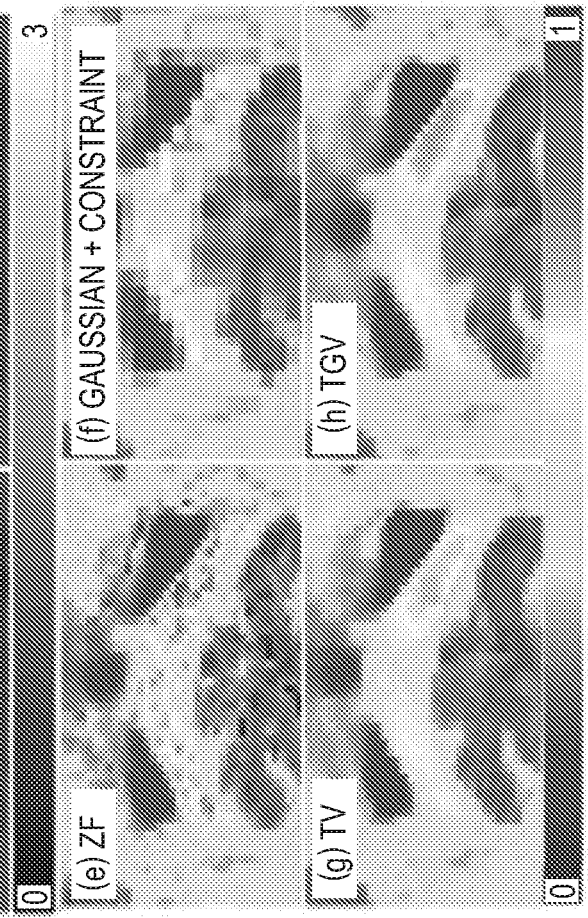
FIG. 5A  FIG. 5B
FIG. 5C  FIG. 5D

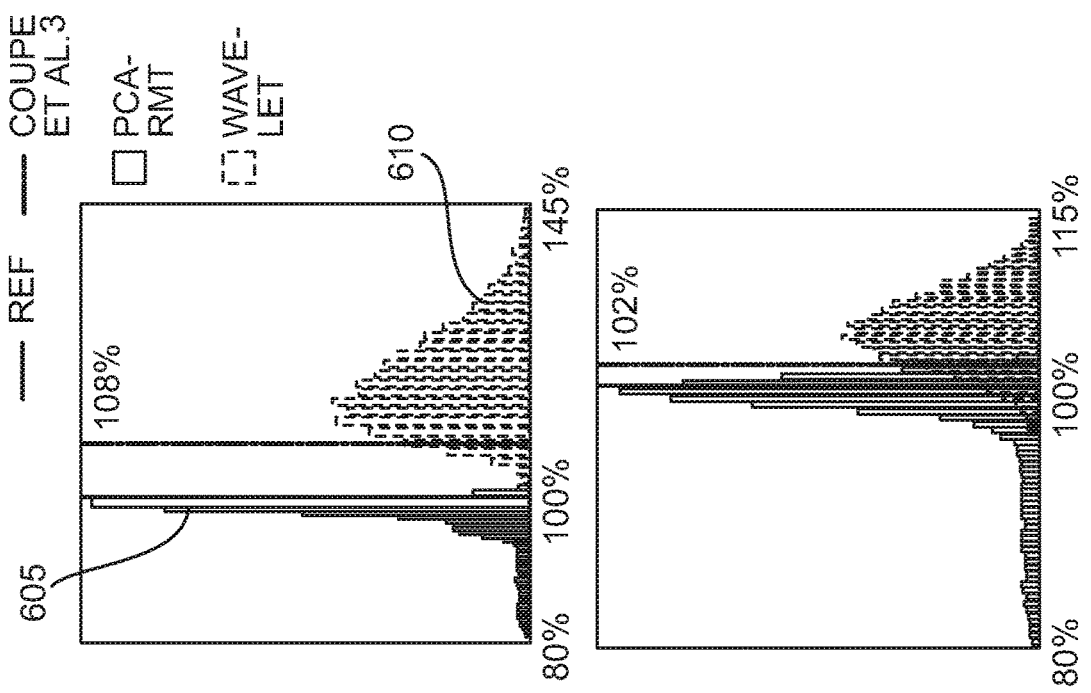
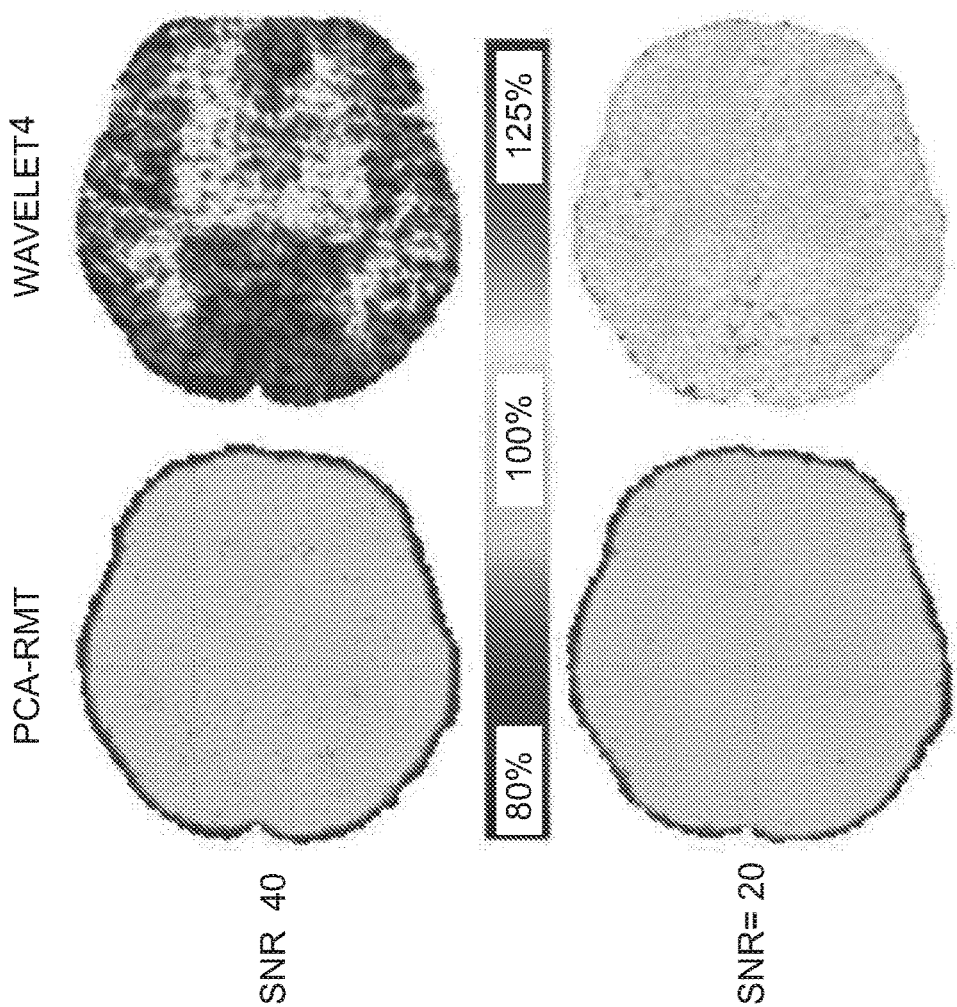
FIG. 6

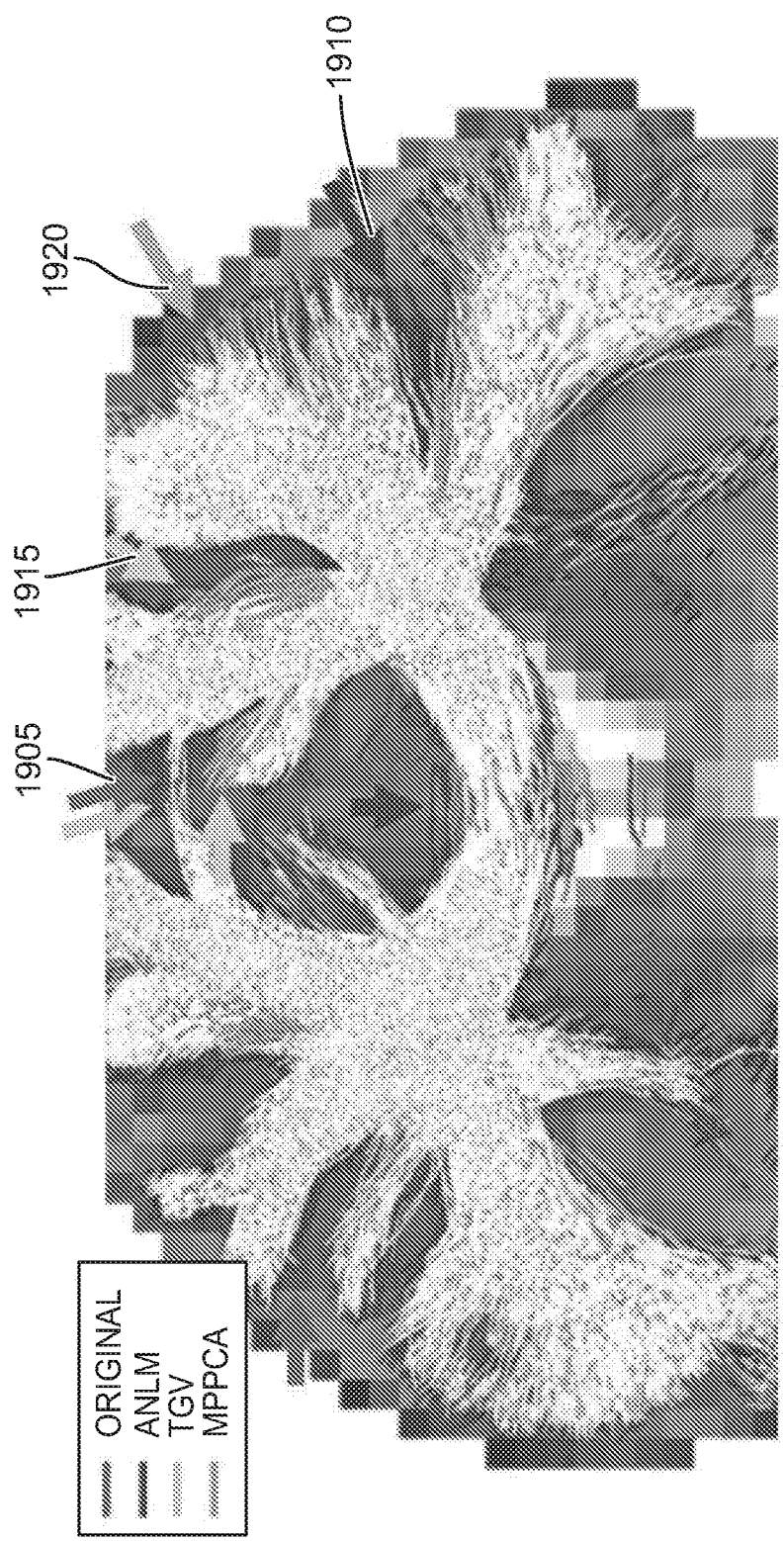

SYSTEM, METHOD AND COMPUTER ACCESSIBLE MEDIUM FOR NOISE ESTIMATION, NOISE REMOVAL AND GIBBS RINGING REMOVAL

CROSS REFERENCE TO RELATED APPLICATIONS

This application relates to and claims the benefit and priority from International Patent Application No. PCT/US2016/032761 filed on May 16, 2016, which relates to and claims priority from U.S. Provisional Patent Application Ser. Nos. 62/162,164, filed on May 16, 2015, and 62/317,061, filed on Apr. 1, 2016, the entire disclosures of which are incorporated herein by reference.

FIELD OF THE DISCLOSURE

The present disclosure relates generally to the suppression of undesired signal fluctuations due to noise and/or Gibbs ringing in one or more images, and more specifically, to exemplary embodiments of exemplary system, method and computer accessible medium for, for example, performing noise estimation and removal, and Gibbs ringing removal from one or more images.

BACKGROUND INFORMATION

Noise and Gibbs ringing that can corrupt magnetic resonance images can, for example, hamper visual and statistical inspection, and processing of the magnetic resonance images and the derived parametric maps.

Thus, it may be beneficial to provide an exemplary system, method and computer-accessible medium for noise estimation and removal, and Gibbs ringing removal, which can overcome some deficiencies present in current magnetic resonance imaging ("MRI") systems.

SUMMARY OF EXEMPLARY EMBODIMENTS

An exemplary system, method and computer-accessible medium for removing Gibbs ringing from a magnetic resonance ("MR") image(s), can be provided, which can include, for example, receiving information related to the MR image(s), and removing the Gibbs ringing from the information by extrapolating data in a k-space from the MR image(s) beyond an edge(s) of a measured portion of the k-space based on a regularized minimization problem(s). A first weighted term of the regularized minimization problem(s) can preserve a fidelity of the measured portion of the k-space, and a second weighted term of the regularized minimization problem(s) can be a penalty term that can be based on a norm(s) of a representation of the MR image(s), which can be presumed to be sparse. A regularization parameter(s) can be selected based on a discrepancy criterion (criteria) that can depend on the noise level. In some exemplary embodiments of the present disclosure, the data can be extrapolated using a second order total generalized variation ("TGV") minimization(s), which can implicitly assume one piecewise linear function.

An exemplary system, method and computer-accessible medium for estimating noise in a first image(s), can be provided, which can include, for example, receiving a plurality of second images, and estimating the noise in the first image(s) based on a principal component analysis ("PCA") procedure on a subset of the plurality of second images. The noise level can be estimated based on a set of eigenvalues resulting from the PCA procedure, and further estimated based on a noise-only distribution of a subset of the eigenvalues, which can be a Marchenko-Pastur distribution.

An exemplary system, method and computer-accessible medium for removing the noise in a first magnetic resonance ("MR") image(s), can be provided, which can include, for example, receiving a plurality of second images, and distinguish between the signal carrying principal components and those principal components that contribute to noise only using a PCA procedure on a subset of the plurality of second images. The Marchenko-Pastur distribution can provide an objective and user independent criterion to distinguish between the signal and noise carrying eigenvalues of, for example, the PCA procedure. The second images can, for example, include diffusion-weighted magnetic resonance images, a set of images obtained from different coils or channels in multichannel MR imaging set-up, or any other plurality of redundant data series.

In some exemplary embodiments of the present disclosure, a threshold between only the noise and at least one principal component of the PCA procedure can be identified. The threshold can be identified based on a noisy covariance matrix(es). The noise can be removed based on the threshold, which can include removing a noise-only component(s) of the first image(s). The noise can be removed using a Marchenko-Pastur distribution(s).

An exemplary system, method and computer-accessible medium for removing Gibbs ringing from a first magnetic resonance ("MR") image(s), can be provided, which can include, for example, receiving a plurality of second MR images, estimating and removing the noise in the first image(s) based on a principal component analysis ("PCA") procedure on a subset of the second images, and removing the Gibbs ringing from the first MR image(s) by extrapolating data in a k-space, based on the noise, from the first MR image(s) beyond an edge(s) of a measured portion of the k-space.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 4(A)-4(D) are exemplary images of the exemplary mean kurtosis of an axial slice of HCP data according to an exemplary embodiment of the present disclosure;

FIG. 5 is a graph illustrating an eigenvalue spectrum of a sample covariance matrix of simulated diffusion-weighted data and Marchenko-Pastur distribution according to an exemplary embodiment of the present disclosure FIG. 6 is set of graphs and signal-to-noise ratio maps based on and/or generated by the exemplary, system and computer-accessible medium according to an exemplary embodiment of the present disclosure;

FIG. 11 A is a set of σ-normalized residual maps for a single diffusion-weighted image according to an exemplary embodiment of the present disclosure;

FIG. 19 is an exemplary image of the overlay of tractograms derived from a single repetition of the $M_{b=2.5}$ data subset before and after denoising according to an exemplary embodiment of the present disclosure;

Figure 1:
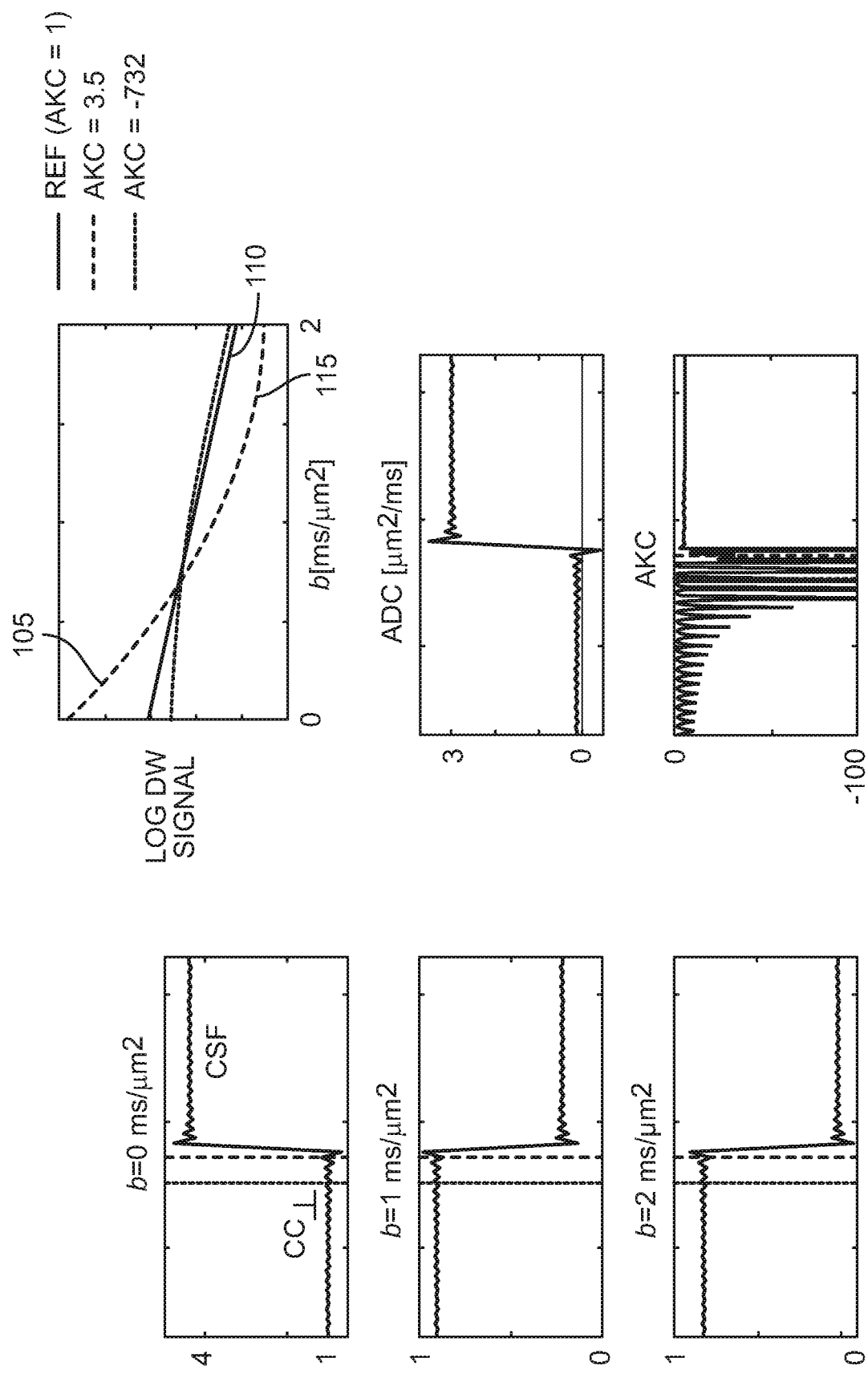
FIG. 1 is a set of graphs illustrating the over- and undershoots of the diffusion and kurtosis coefficients according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

MR images can be affected by the Gibbs ringing that can appear near sharp edges, due to truncation of the k-space. While introducing a bias of about 9% in the weighted images, the Gibbs effect can be amplified tremendously in the derived parametric maps, for example, in diffusion and kurtosis tensor components. The amplification can occur because the Gibbs oscillations in the b=0 and finite-b images can be out of phase due to relative difference in DW signal, S(b), and intensities at different b-values. FIG. 1 illustrates this phenomenon for realistic values on the cerebral spinal fluid ("CSF")-Corpus Callosum border with diffusion and kurtosis estimated in the radial direction. This can create a concave (e.g., FIG. 1 element 115), rather than convex (e.g., FIG. 1 elements 105 and 110), log S(b), which can lead to extreme unphysical apparent diffusion coefficient ("ADC") and apparent kurtosis coefficient ("AKC") values. The fits can exceed the physically expected bounds (e.g. positive diffusivity and kurtosis), resulting in the "black voxels" (see, e.g., FIG. 4A). Thus far, the Gibbs ringing bias has been ignored or reduced by isotropic smoothing at the expense of spatial resolution loss, and the introduction of partial volume effects. However, the exemplary system, method and computer-accessible medium, according to an exemplary embodiment of the present disclosure, can extrapolate the data in k-space beyond the maximally measured cutoff value $k_c$ by using, for example, a second order total generalized variation ("TGV") minimization (see, e.g., Reference 1), which can substantially reduce Gibbs ringing and noise of the MRI data, without compromising the resolution. To perform such an exemplary procedure, the exemplary system, method and computer-accessible medium, according to an exemplary embodiment of the present disclosure, can depend on the independent determination of the noise level, such as the estimation procedure described below.

The exemplary system, method and computer-accessible medium, according to an exemplary embodiment of the present disclosure, can estimate a spatially varying noise level (e.g., can plot the noise map) from a series of MR images in a model-independent way. As the noise in MR can generally be non-Gaussian, the importance to correct for, for example, Rician or non-central $\chi$ noise bias, can rely on an independent unbiased estimate for the noise map. Estimating the noise can be challenging as MR images can suffer from low spatial resolution and involuntary motion. Moreover, the noise can generally be spatially varying due to the use of parallel imaging techniques. This can be the reason why noise estimation has remained a challenging problem, with only a few methods able to deal with the spatially varying nature of the noise.

The prior techniques depend on signal model assumptions, or the wavelet transformation, to decompose the data in low frequency ("signal") and high frequency ("noise") information. Wavelet-based methods tend to overestimate the noise level, as the high frequency sub-band can also contain residual signal due to actual sharp edges in the image. Physiological noise, image misalignment and model inaccuracies, all tend to bias the model-based methods. In contrast, the exemplary system, method and computer-accessible medium, according to an exemplary embodiment of the present disclosure, can provide and/or facilitate a local noise estimation paradigm based on the random matrix theory ("RMT") result for random covariance matrices. (See, e.g., Reference 8). The exemplary system, method and computer-accessible medium, according to an exemplary embodiment of the present disclosure, can be free of, and perform better than, the above prior systems and methods. For example, principal component analysis ("PCA"), coupled with RMT, can be used to exploit the redundancy in a MR data series for the robust, accurate, and precise estimation of the noise level in a number of MRI modalities, such as diffusion, perfusion, functional MRI, T2, and T2*, etc.

The exemplary system, method and computer-accessible medium, according to an exemplary embodiment of the present disclosure, can remove the noise by exploiting the fact that noise-only eigenvalues of a PCA can be expected to be described by the universal Marchenko-Pastur distribution, a result of the random matrix theory for noisy covariance matrices. (See e.g., Reference 36). Nullification of all eigenvalues smaller than a threshold that can be a property of the Marchenko-Pastur distribution corresponding to suppression of the noise. The threshold can depend on the noise level, which can be estimated by evaluating the eigenspectrum using, for example, the Marchenko Pastur distribution. Therefore, one might correct the denoised signal for Rician or non-central-$\chi$ distributed noise bias (see e.g., References 37 and 38) using the method of moments, which rely one the noise level. (See e.g., Reference 39). Furthermore, the exemplary system, method and computer-accessible medium, according to an exemplary embodiment of the present disclosure, can preserve the underlying signal better than other techniques on the level of the diffusion sensitized images and diffusion MR parameters of general interest.

Exemplary Method

The exemplary system, method and computer-accessible medium, according to an exemplary embodiment of the present disclosure, can extrapolate k-space data beyond the measured k-space edge $k_c$, in order to remove undesired signal fluctuations due to noise and Gibbs ringing. The extrapolation of the k-space can be formatted as a regularized minimization problem $\hat{u}=\arg\min_u \|\tilde{\mathcal{F}}u-\tilde{k}\|_2^2 + \lambda \mathcal{R}(u)$. The 1$^{st}$ term can preserve the fidelity with the acquired data $\tilde{k}$ (e. g., here, $\tilde{\mathcal{F}}$) can be the windowed Fourier transformation), and the penalty term $\mathcal{R}(u)$ can be based on the $L_1$ norm of the image u in the basis where it can be presumed to be sparse, with a regularization parameter $\lambda$ chosen according to the discrepancy criterion. (See, e.g., Reference 4). This exemplary criterion can include the noise level as an input. This noise level can be estimated, for instance, using a redundancy of oversampled data as described below, or using any suitable noise estimation method. (See, e.g., Reference 11). A challenge can be to find the "right" sparse basis. The second order TGV function (see, e.g., Reference 5): $\mathcal{R}(u) = \arg\min_v a\int_\Omega \|\nabla u-v\|_1 dx + b\int_\Omega \|\nabla v\|_1 dx$ can be evaluated where v can be a vector field within a volume or a slice, whose components can be bounded by 0 and $\nabla u$, and compare it to the more commonly used TV. The empirical parameters a and b can be set to, for instance, 2 and 1, respectively. (See, e.g., References 2 and 3). Unlike TV, the second order TGV can sparsify piecewise linear functions. The reduced penalty term for this non-constant piecewise linear function can avoid the staircasing effect, which can often be observed in TV regularization. An exemplary primal dual procedure can be used to solve the optimization problem. (See, e.g., Reference 6).

Figure 8A:
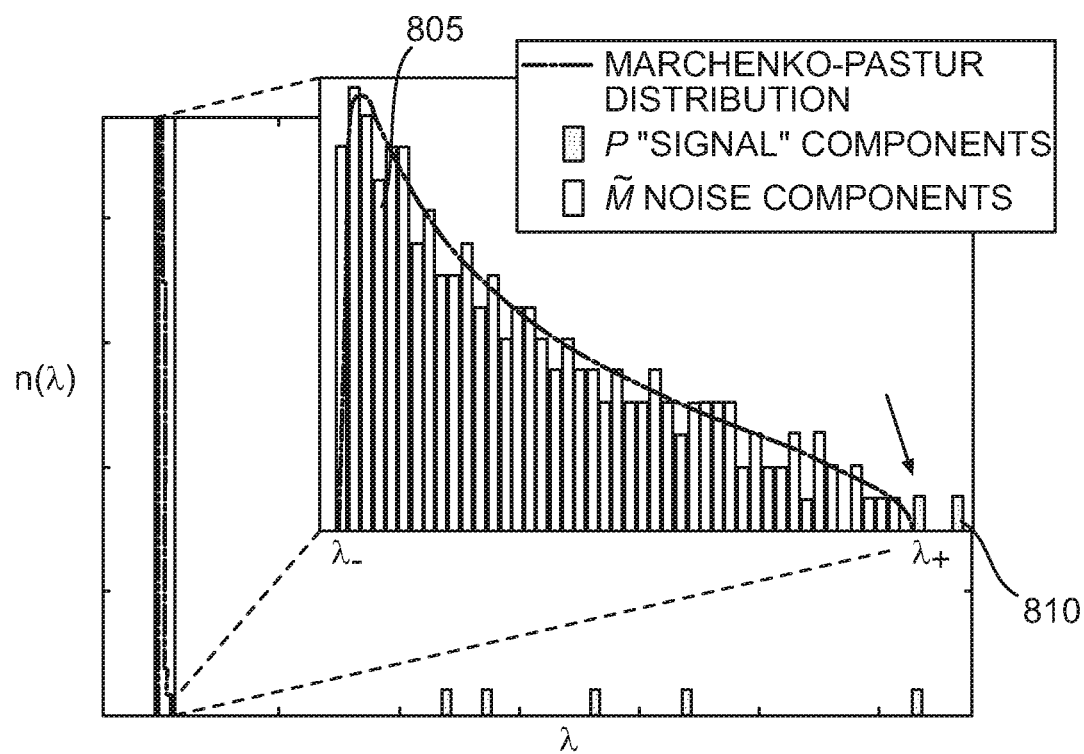
FIG. 8A is an exemplary graph of a Marchenko Pastur distribution according to an exemplary embodiment of the present disclosure.
Figure 8B:
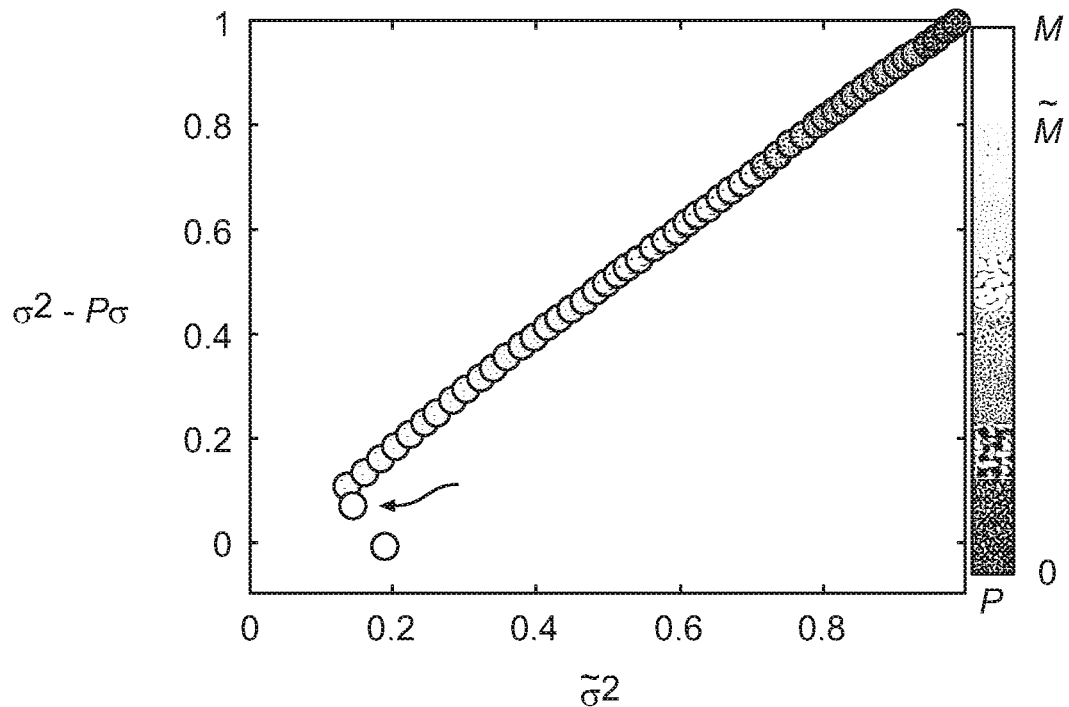
FIG. 8B is an exemplary graph of the contribution of signal and noise eigenvalues to data variability according to an exemplary embodiment of the present disclosure.

The exemplary system, method and computer-accessible medium, according to an exemplary embodiment of the present disclosure, can be used to separate signal from noise without being dependent on an often unknown physical model of the signal, which can be performed utilizing the coupling of a PCA with RMT. If the noise-free signal can be characterized by only a small number P<<N,M of parameters, compared to the number M of diffusion acquisitions and number N of voxels, a lot of redundancy can be expected in the data—even if both the model and its parameters can be unknown. For example, PCA based on the singular value decomposition of the M×N matrix can typically show a few "significant" eigenvalues, and the vast majority of the others originating due to the noise. Unfortunately, distinguishing between the "significant" and "noise" eigenvalues can be far from trivial. While noise in each diffusion direction can be random, its contribution to the histogram of covariance matrix eigenvalues can become deterministic for N,M>>1. (See, e.g., FIG. 8a). In the case of the noise realized via independent identically distributed random variables in each channel (e.g. each imaging voxel), the contribution of the noise to the histogram of the PCA eigenvalues can be given by the universal Marchenko-Pastur distribution (see, e.g., Reference 8), where, for example:

$$p(\lambda) = \frac{\sqrt{(\lambda_+ - \lambda)(\lambda - \lambda_-)}}{2\pi Q \sigma^2} \text{ if } \lambda_- \leq \lambda \leq \lambda_+ \text{ (0 otherwise)}$$

with $\lambda_\pm = \sigma^2(1\pm\sqrt{Q})^2$, $\sigma$ the standard deviation of the noise in each channel (e.g. imaging voxel), and $Q=\tilde{M}/N$ ($\tilde{M}$ can be the number of noise-only components). When the noise in each channel (e.g., imaging voxel) can be characterized by a variance, not necessarily the same for each channel, a generalization of the Marchenko-Pastur distribution can be obtained, analytically or numerically, which can be parameterized by a set of noise variances The unknown parameters, $\sigma$ and $\tilde{M}$, can, for example, be estimated by exploiting the following or other properties of the Marchenko-Pastur distribution: (i) the expectation value of the distribution is proportional to $\sigma^2$, and (ii) the width of the Marchenko-Pastur distribution is proportional to $\sigma^2$. Thus, the average and range of the $\tilde{M}$ smallest eigenvalues can be proportional to $\sigma^2$. To correct for the potential of non-Gaussian MR data statistics, the "significant" eigenvalues, which can be determined as being above the edge of the bulk of the noise-only eigenvalues, can be used to estimate the underlying signal. Both this signal, and the Gaussian noise level(s) $\sigma$, can return the non-Gaussian noise level(s) using, for example, Koay's inversion procedure. (See, e.g., Reference 9). The exemplary system, method and computer-accessible medium, according to an exemplary embodiment of the present disclosure, can apply this procedure within a sliding window (e.g., N=7×7×7), or in any other suitable manner of combining N voxels.

The exemplary system, method and computer-accessible medium, according to an exemplary embodiment of the present disclosure, can be used to estimate the noise level, for example, based on a grid search in function of $\tilde{M}$ to identify the subset of $\tilde{M}$ smallest eigenvalues that can meet the above-described, or complementary, properties of the Marchenko-Pastur distribution. Thus, the exemplary system, method and computer-accessible medium, according to an exemplary embodiment of the present disclosure, can combine the estimation of the noise level to adjust the regularization parameter $\lambda$ utilized in the exemplary Gibbs ringing removal procedure. In particular, the optimally adjusted $\lambda$ can, for example, preserve the data fidelity up to level of the noise variance scaled by the number of measured k-space samples.

The exemplary system, method and computer-accessible medium, according to an exemplary embodiment of the present disclosure, can be used to remove the noise of a redundant data matrix X, for example, based on a grid search in function of $\tilde{M}$ to identify the subset of $\tilde{M}$ smallest eigenvalues that can meet the above-mentioned, or complementary, properties of the Marchenko-Pastur distribution. Nullifying the $\tilde{M}$ smallest eigenvalues, and reconstructing the matrix, can result in a denoised matrix, where, for example: $\hat{X}=\sqrt{N}U\tilde{\Lambda}V^T$, with U and V unitary matrices whose columns can be the left-singular and right-singular vectors of the redundant data matrix X, respectively, and $\tilde{\Lambda}$ a diagonal matrix of the corresponding eigenvalues where the $\tilde{M}$ smallest eigenvalues can be set to zero. Since the exemplary system, method and computer-accessible medium, according to an exemplary embodiment of the present disclosure, can simultaneously output the denoised data and noise variance, the denoised data can, for example, be corrected for the Non-Gaussian noise biases using, for example, Koay's inversion procedure. (See, e.g., Reference 9). The exemplary system, method and computer-accessible medium, according to an exemplary embodiment of the present disclosure, can apply this procedure within a sliding window (e.g., N=7×7×7), or in any other suitable manner of combining N voxels.

Exemplary Simulation: Gibbs Ringing Removal

Figure 2:
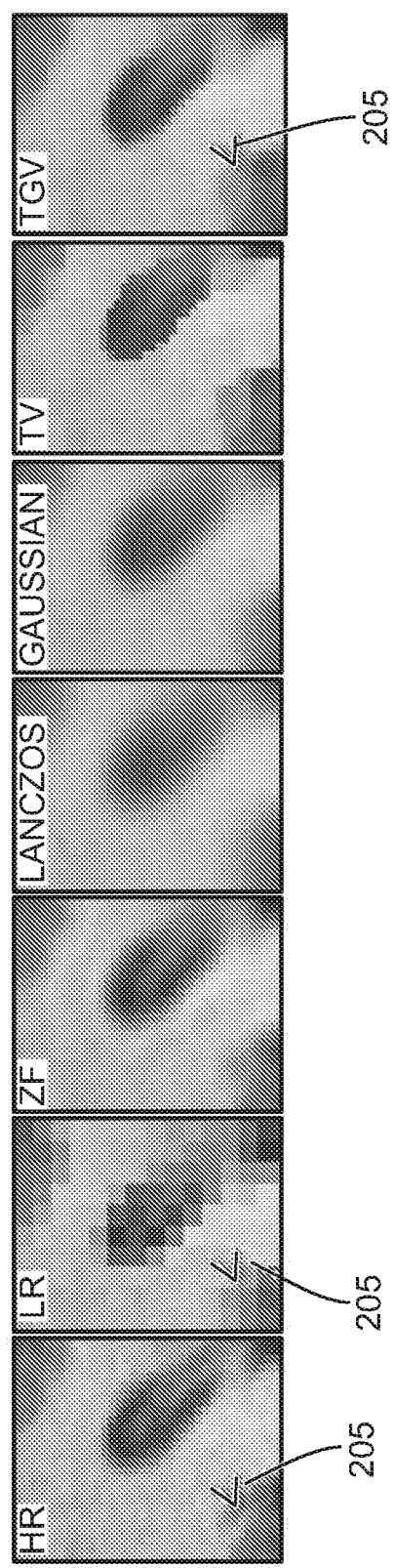
FIG. 2 is a set of reconstruction MPRAGE images generated using the exemplary system, method and computer-accessible medium according to an exemplary embodiment of the present disclosure.
Figure 3:
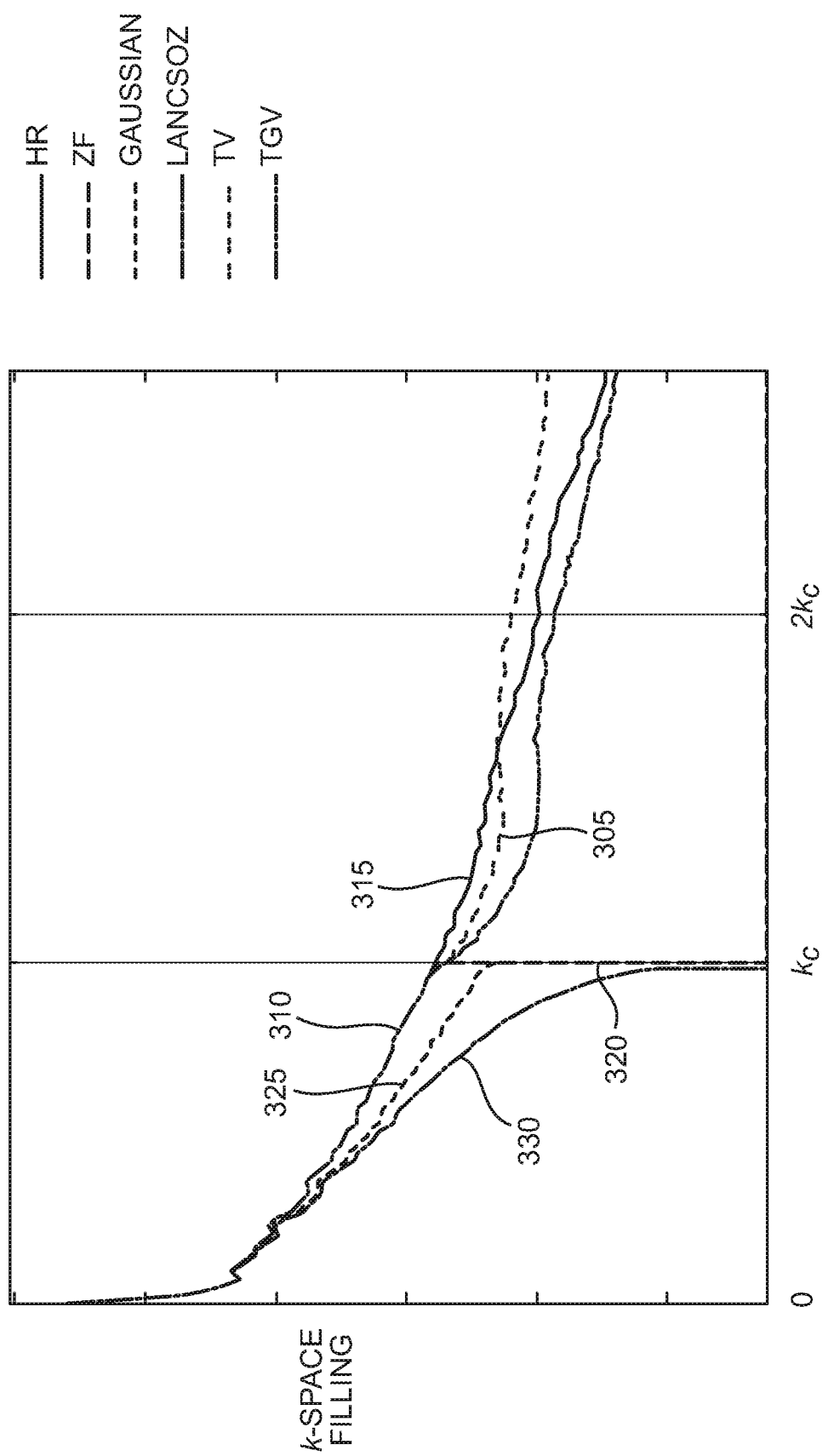
FIG. 3 is a graph illustrating k-space energy density as function of the distance to the k-space center according to an exemplary embodiment of the present disclosure.
Figure 5:
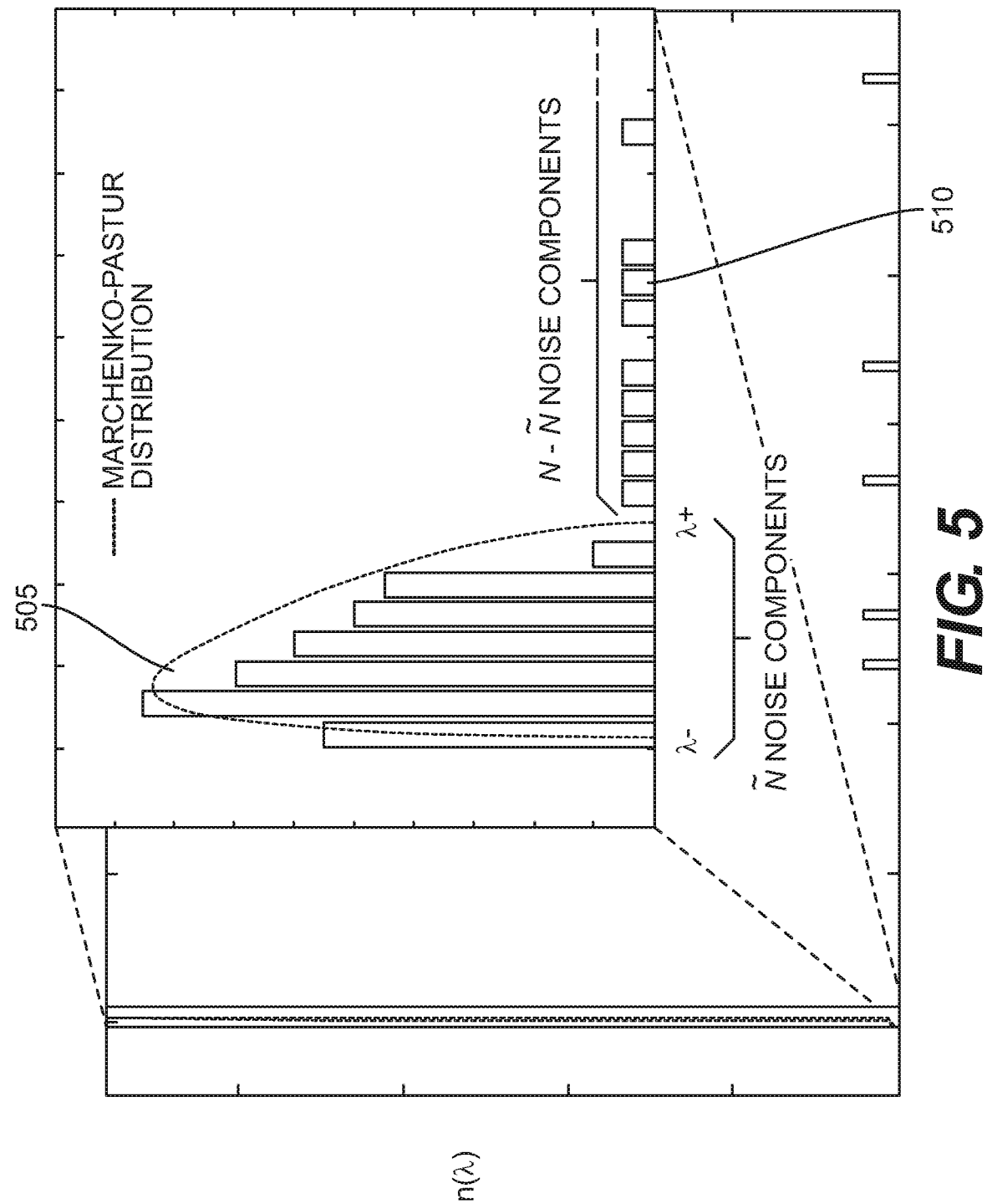
FIGS. 5 (A)-4(D) are exemplary images of an axial slice of HCP data according to an exemplary embodiment of the present disclosure.

Truncating a high-resolution (e.g., HR; 256×256) MPRAGE image in k-space (e.g., cut-off frequency $k_c$) generated a simulated image that mimics a low-resolution "acquisition" (e.g., LR; 96×96). A qualitative comparison of the different filtering and reconstruction procedures, for example, zero-filling ("ZF"), TV and TGV, applied on the single slice of a simulated image shows that Gibbs ringing can be strongly reduced by extrapolation of the k-space using second order TGV without the introduction of the staircase or loss of spatial resolution compared to LR acquisition. (See, e.g., FIG. 2). However, fine anatomical details lost during LR acquisition cannot be recovered (see, e.g., FIG. 2, arrows 205). This can be expected, as there may be no random sampling in the HR k-space for the compressed sensing reconstruction to work. Both the Lancsoz and Gaussian filters show significant spatial resolution loss. As shown in the graph of FIG. 3, corresponding k-space filling, for example, the k-energy density as function of the distance to the k-space center shows that in contrast to window filtering, both TV (line 305) and TGV (line 310) hardly affect the actually measured k-space data, k<$k_c$. A good recovery of k-space filling beyond $k_c$ for both TV and TGV can be observed. The broad peak at k~2$k_c$ can be a signature of the nonlinear reconstruction (e.g., harmonic doubling). TV's overestimation of high frequencies compared to the HR (line 315) data can explain the staircase artifact observed in the corresponding image, as it can model the image as a piecewise constant function. (See, e.g., References 2 and 3). The TGV reconstructed images do not show the staircase artifacts. The graph of FIG. 3 also illustrates measure k-space data for ZF (line 320) Gaussian (line 325) and Lancsoz (line 330)

Exemplary Simulation: Noise Estimation

FIG. 6 shows a set of maps and graphs estimated from simulated data (e.g., average SNR of the non-DW image was 20 and 40). Noise-free (e.g., filtered) DW images (e.g., 90 gradient directions and b=1 ms/µm²) were derived from Human Connectome Project dMRI data by fitting 4th order spherical harmonics and recomputing directional data; this can be used as ground truth. Rician noise with a uniform noise level was artificially added to compare the exemplary proposed local RMT-based method (e.g., PCA-RMT element 605), local wavelet-based noise map estimator (see, e.g., Reference 11) ("WAVELET") (e.g., element 610), and its global counterpart. (See, e.g., Reference 10). Both wavelet approaches tend to overestimate the noise; this bias can depend on SNR. Moreover, its local version (see, e.g., Reference 11) shows structure, whereas the exemplary RMT method can show high accuracy and precision regardless of the underlying signal.

Exemplary Denoising Simulation

Figure 9:
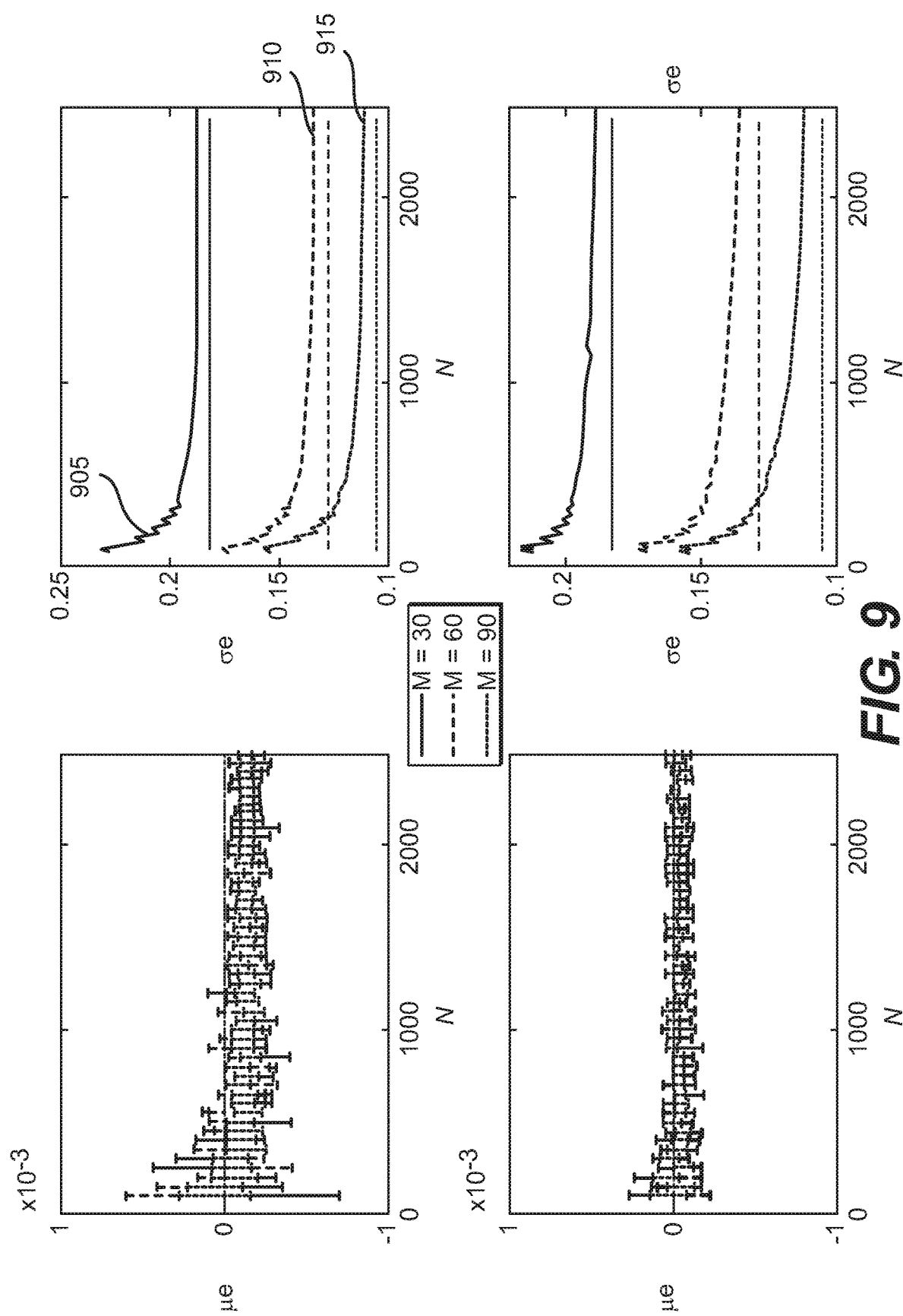
FIG. 9 is a set of graphs of a percent bias in the estimation of the free-noise signal according to an exemplary embodiment of the present disclosure.

A set of 1000 Rician distributed M×N data matrices was computed by projecting N, ranging from about 100 to about 2500, axially symmetric diffusion tensors onto M=30, 60, and 90 diffusion gradient directions with b=1 ms/µm². The underlying FA and MD for each tensor was sampled from a distribution with mean 0.6 and 0.8 µm²/ms, respectively, and standard deviation of 0.1. The accuracy of the denoising procedures, as a function of M and N, can be evaluated. In FIG. 9, the average and standard deviation of the error, that can be the difference between denoised and noise-free signal, can be plotted as function of M, N and SNR. As shown in the graphs of FIG. 9, M can equal 30 (e.g., element 905), 60 (element 910) or 90 (element 915). The overall accuracy of denoising can be very high. The error, normalized by noise-free data, can be unbiased with a significance of α=0.05 for SNR=50, whereas the underestimation of the signal for SNR=25 can be limited to about 0.01% after Rician bias correction. The standard deviation of the error, that can be the standard deviation of the non-suppressed noise, normalized by $\sigma\sqrt{p}$, can decay with M and N, $$\sim \sqrt{\frac{M}{P}} \text{ for } N \to \infty.$$

A universal expression of the decay for finite N can be missing though.

Exemplary Diffusion-Weighed MR: Noise Estimation

Figure 7:
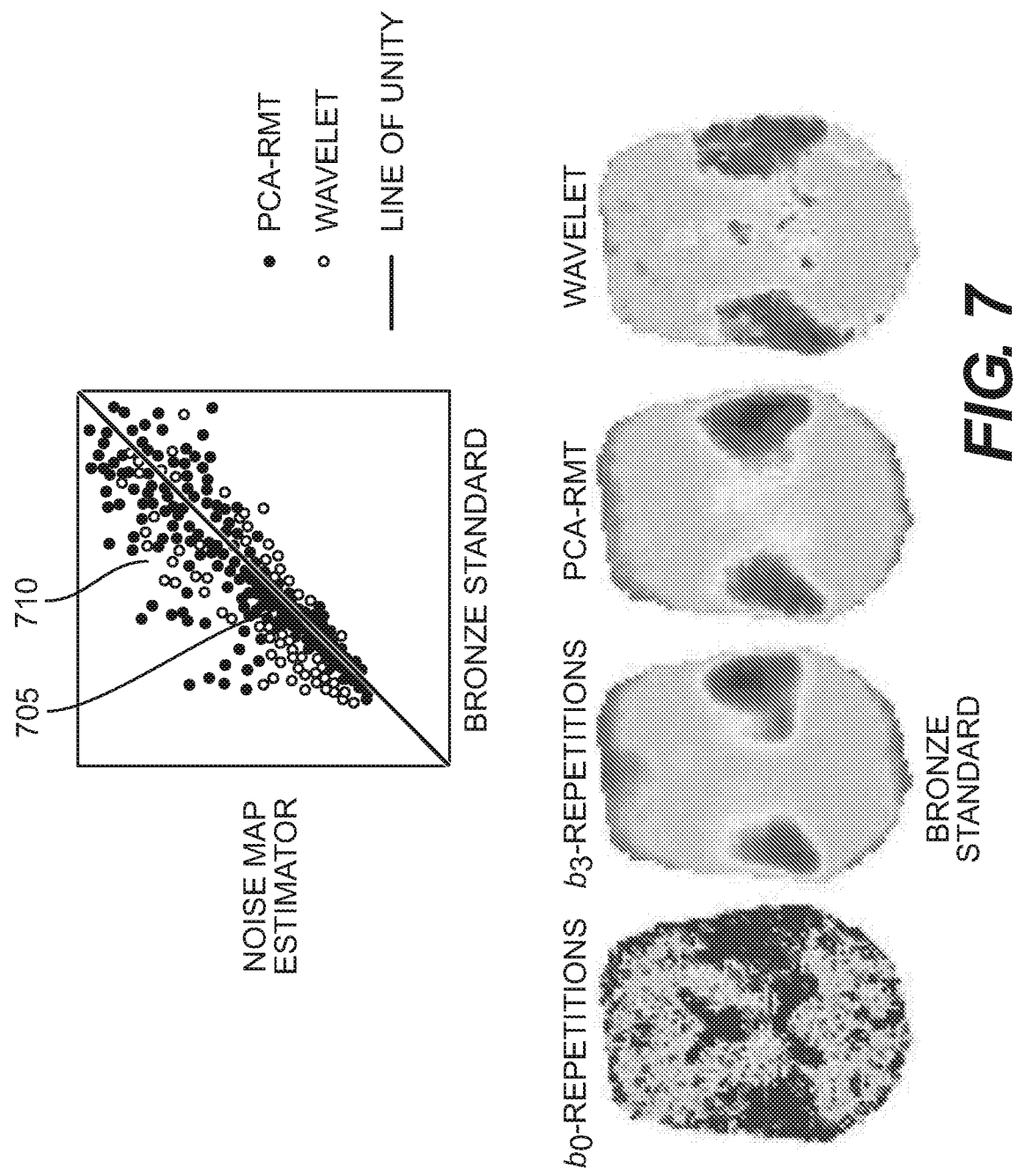
FIG. 7 is a set of maps illustrating exemplary results produced by the exemplary system, method and computer-accessible medium according to an exemplary embodiment of the present disclosure compared to a previous method.

Diffusion-weighted MR data can be selected as an example of a redundant MR series. For a diffusion-weighted MR measurement (e.g., 12 repetitions of b=0, 60×b=1 ms/µm², 12 repetitions of 1×b=3 ms/µm²), the exemplary system, method and computer-accessible medium, according to an exemplary embodiment of the present disclosure, can be applied to the b=1 ms/µm² shell, and can be compared to (i) the wavelet-based local noise map estimator applied on the same shell, and (ii) the noise maps derived from the repeated measurements. (See, e.g., FIG. 7). (See, e.g., Reference 12). For example, the graph of FIG. 7 shows the Bronze Standard versus noise map estimators for PCA_RMT 705 and WAVELET 710. The noise map derived from the b=0 repetitions can be affected by pulsation artifacts. This effect may not be visible in the exemplary bronze standard based on 12 repetitions from the same b=3 ms/µm² image. Strong edges (e.g., high frequency information) in the dMRI images shine-through in the wavelet-based approach, whereas the exemplary system, method and computer-accessible medium shows a smooth, artifact-free, noise map that can be more consistent with the bronze standard than the wavelet-based method (e.g., correlation coefficient of 0.9951 and 0.9782, respectively; and FIG. 3).

Exemplary Diffusion-Weighted MRI: Gibbs Ringing Removal

Figure 10:
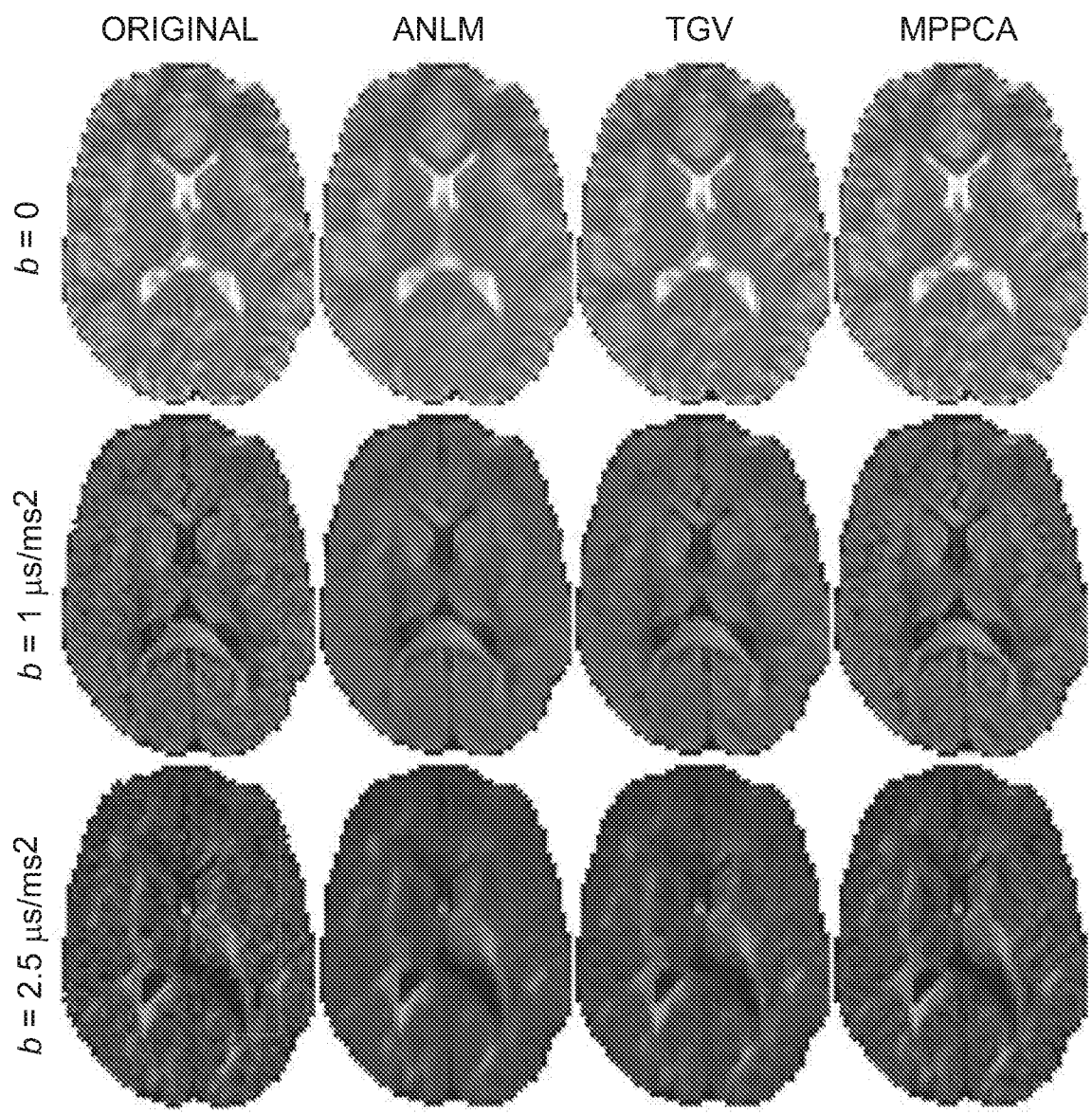
FIG. 10 is a set of exemplary denoised diffusion-weighted images according to an exemplary embodiment of the present disclosure.
Figures 11A, 11B:
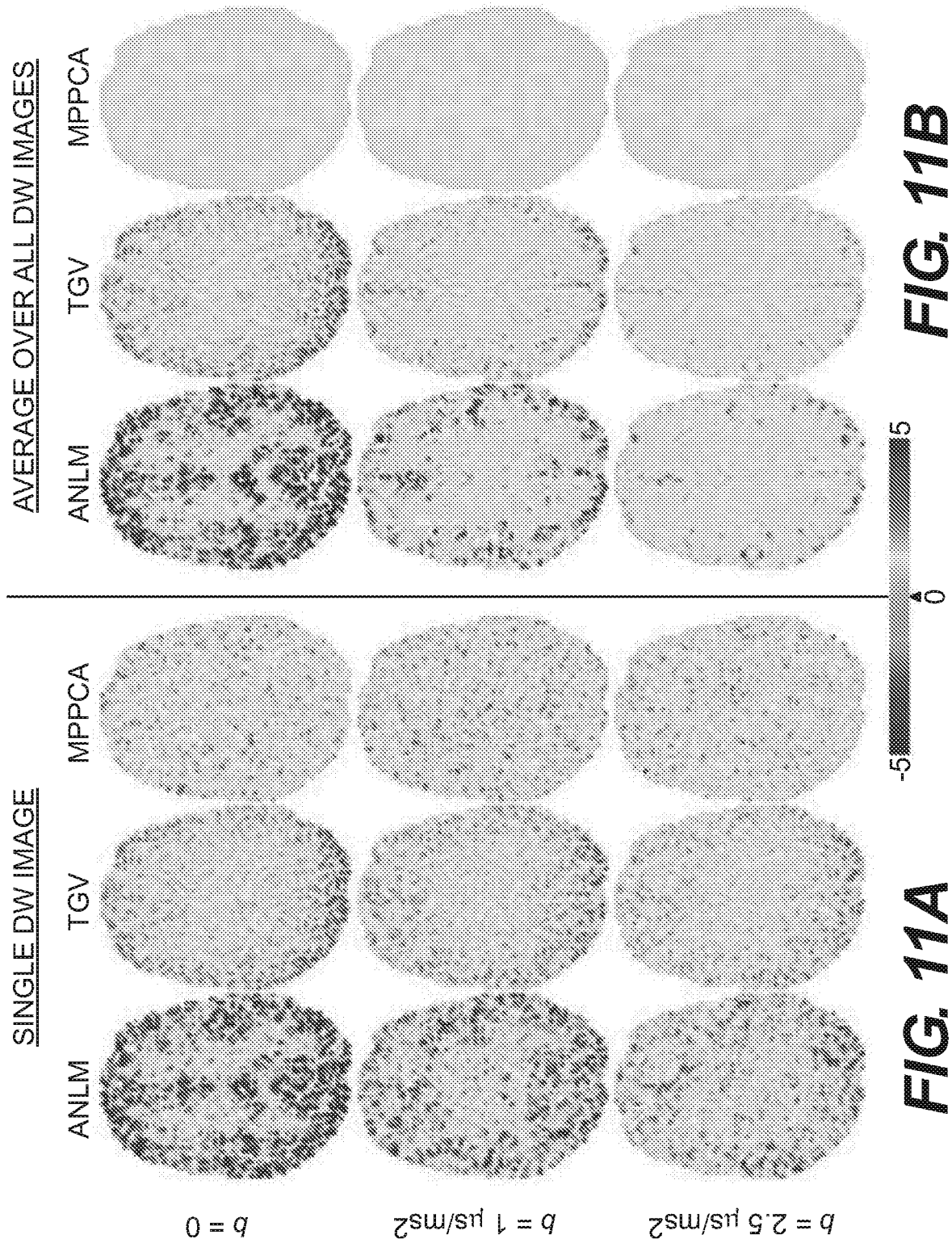
FIG. 11B is a set of σ-normalized residual maps for an average of all diffusion-weighted images according to an exemplary embodiment of the present disclosure.

FIGS. 4(A)-4(D) show mean kurtosis ("MK") images and FIGS. 5A-5D show axonal water fraction ("AWF") images of a detail, for example, the splenium, of a single axial slice of the Human Connectome Project ("HCP") data, which was downsampled to 96×96 by truncation of the k-space and subsequently reconstructed to the original 144×174 resolution using ZF, TV, and TGV. (See, e.g., Reference 7) Without smoothing and constraining the kurtosis tensor fit, extreme negative MK values (e.g., "black voxels") and/or unexpected heterogeneity in AWF can be observed in regions of interest such as the Corpus Callosum. (See, e.g., FIG. 4(A)). Current practice can be to smooth and constraint the data fit. (See, e.g., FIGS. 4(B) and 5 (B)). Both TV (see, e.g., FIGS. 4(C) and 5 (C)) and TGV (see, e.g., FIGS. 4(D) and 5 (D)) result in a more robust fit as they minimize the Gibbs effect and the noise without manipulation of the resulting statistics and loss of spatial resolution. The exemplary regularization parameter can be chosen according to a various criteria based on the noise level, which can be estimated using the exemplary system, method and computer-accessible Exemplary Diffusion-Weighted MRI Noise Removal A healthy volunteer underwent imaging on a Siemens Prisma (e.g., 3T) MR scanner (e.g., Siemens A G, Siemens Medical Solutions, Erlangen, Germany) after obtaining informed consent, using a 64-channel receiver head coil. The body coil was used for transmission. An EPI-DW sequence was used to acquire 3 repetitions of the following dMRI data. Besides the acquisition of about 18 non-diffusion-weighted images, diffusion weighting was applied along about 90 isotropically distributed gradient directions with b=1 and 2.5 ms/µm². The following imaging parameters were kept constant throughout the data acquisition sequences: TR/TE: 4000/76 ms, matrix: 92×92, voxel dimensions: 2.5×2.5 mm, slice thickness: 2.5 mm, slices: 50, parallel imaging factor: GRAPPA with acceleration factor 2, reconstructed using the adaptive combine procedure and simultaneous multislice factor 2. The subsets of this data can be referred to as follows: $M_b$=x=y or $M_{b \le x}$=y, with y the subset s number of dMRI encodings and x an experiment-specific b-value. The exemplary system, method and computer-accessible medium, according to an exemplary embodiment of the present disclosure, can be applied to subset $M_{b \le 2.5}$=120 of the first repetition and can compare the result to ANLM and TGV. The resultant maps for a single dMRI image of b={0, 1, 2.5} ms/µm² are shown for qualitative comparison in FIG. 10. The normalized residuals for those images, r=($\hat{X}$−X)/$\hat{\sigma}$, are shown in FIG. 11A. Although the anatomical structure can already be observed in the residual maps, normalized by noise map, of ANLM and TGV, these effects can mainly be visible after averaging the residual maps of all images per b value. (See, e.g., FIG. 11b). The lack of anatomical structure and zero-centered residuals can indicate good preservation of signal, and/or accuracy. The exemplary MPPCA outperforms ANLM and TGV in that respect.

Figure 12:
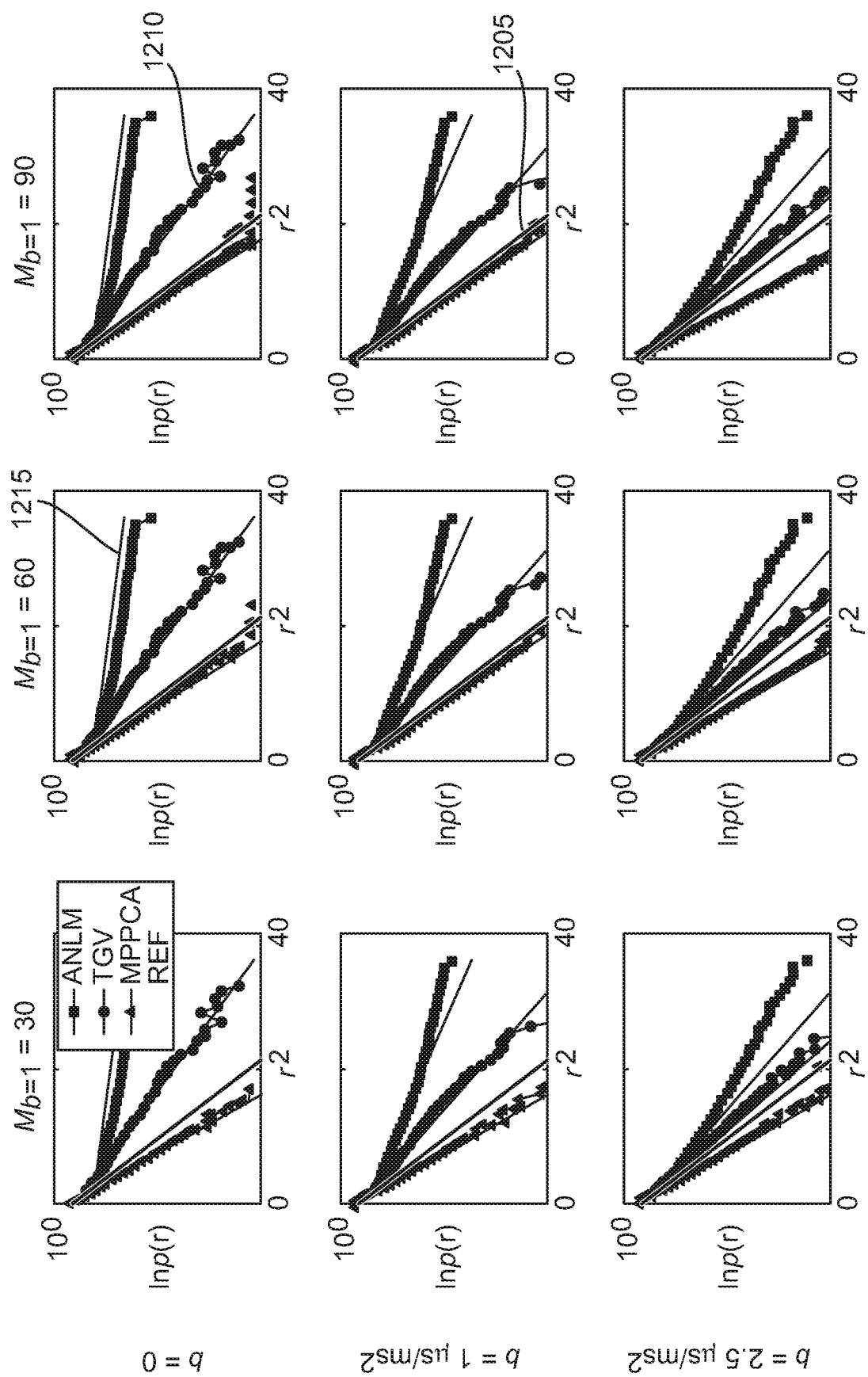
FIG. 12 is a set of graphs of the logarithms of the distribution of normalized residuals p(r) as function of $r^2$ for different b-values according to an exemplary embodiment of the present disclosure.

The distribution of the σ-normalized residuals, r, resulting from denoising following subsets $M_{b=1}$=30, 60, and 90 of the first repetition of the clinical data are shown in FIG. 12. The logarithm of the distribution p(r) can be shown as function of $r^2$. A zero-centered normal distribution with variance $\sigma^2$ can then be represented by a straight line with slope $1/\sigma^2$. Normalized residuals can be described by the standard normal distribution because only then all the noise can be accumulated in the residuals. The exemplary MPPCA (e.g., element 1205) and TGV (e.g., element 1210) can be well described by a normal distribution, whereas ANLM (e.g., element 1219) shows clear deviations. More importantly, MPPCA has a lower variance than unity, whereas TGV and ANLM have a higher variance. In the latter, the residuals contain more variance than explained by the noise. Genuine signal fluctuations (e.g. fine anatomical details) can be removed by ANLM and TGV and add to the variance of the residuals. Conversely, MPPCA does not remove anatomical details; conservatively removing only noise. The variance of the exemplary MPPCA residuals can range from about 68% to about 89% of the estimated noise variance. This translates to an MPPCA induced SNR improvement of about 76% and about 200%, respectively.

Figure 13:
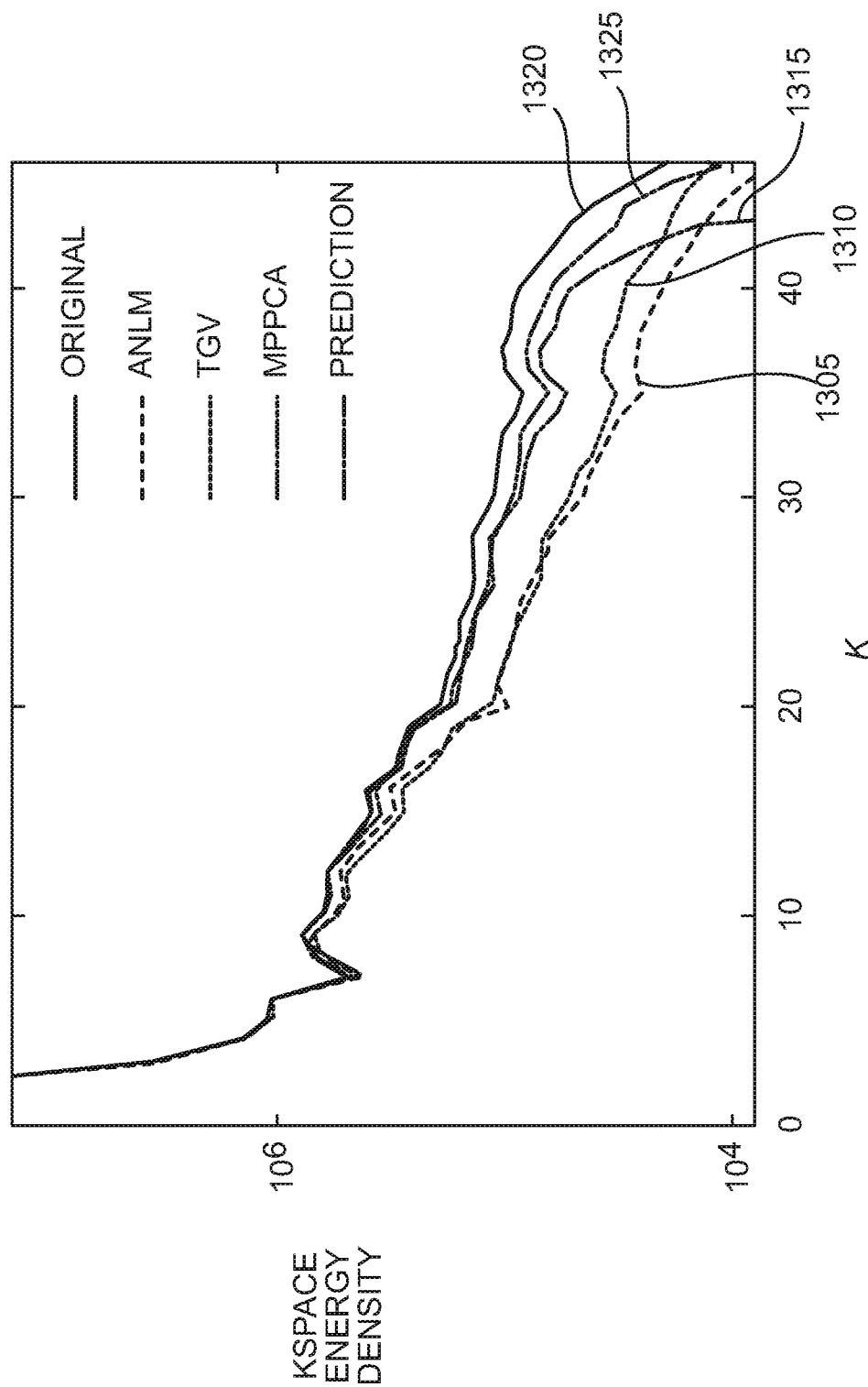
FIG. 13 is a graph of k-space energy density as function of the distance to the k-space center according to an exemplary embodiment of the present disclosure.
Figure 14:
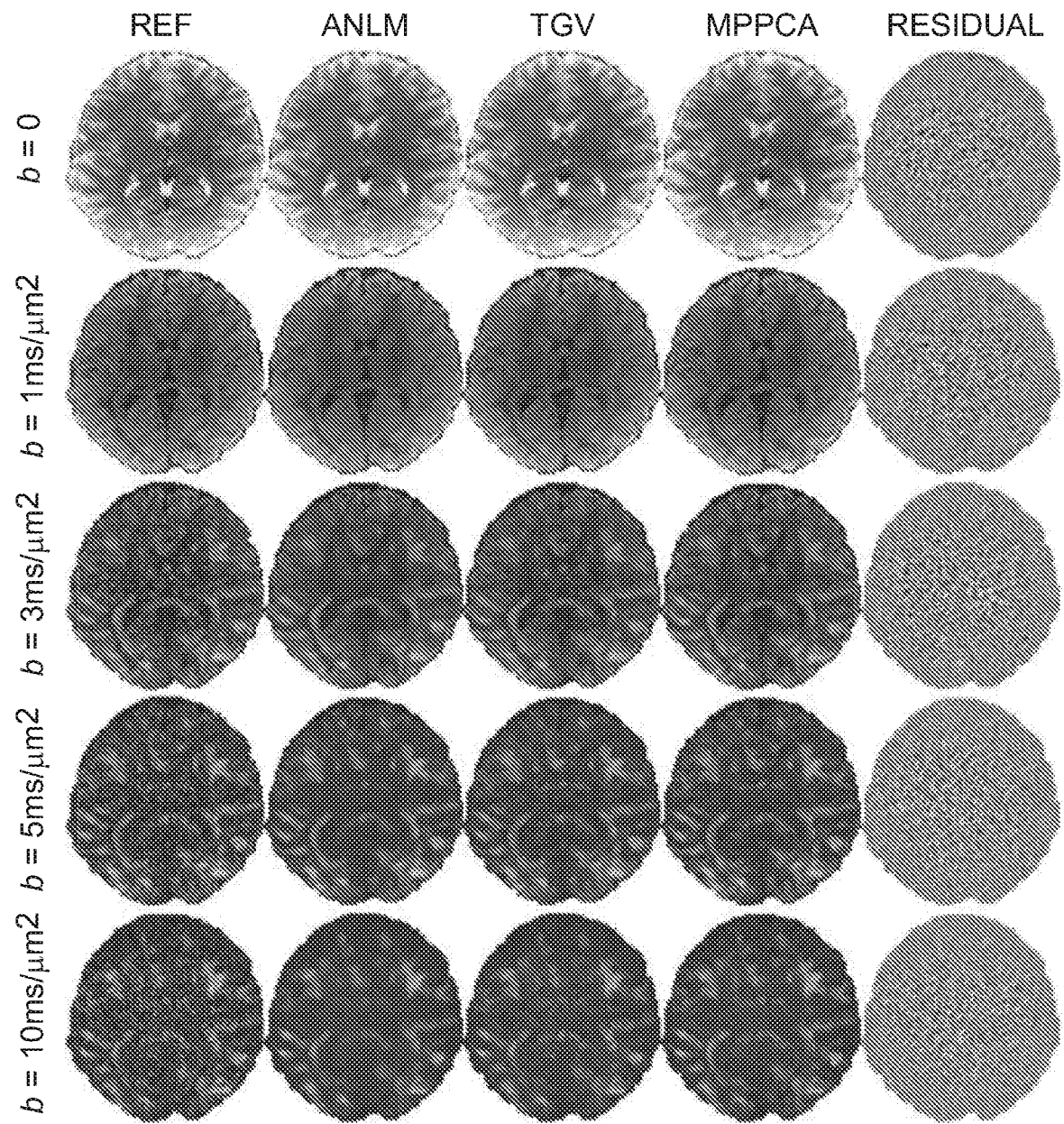
FIG. 14 is a further set of denoised diffusion-weighted images according to an exemplary embodiment of the present disclosure.
Figure 15:
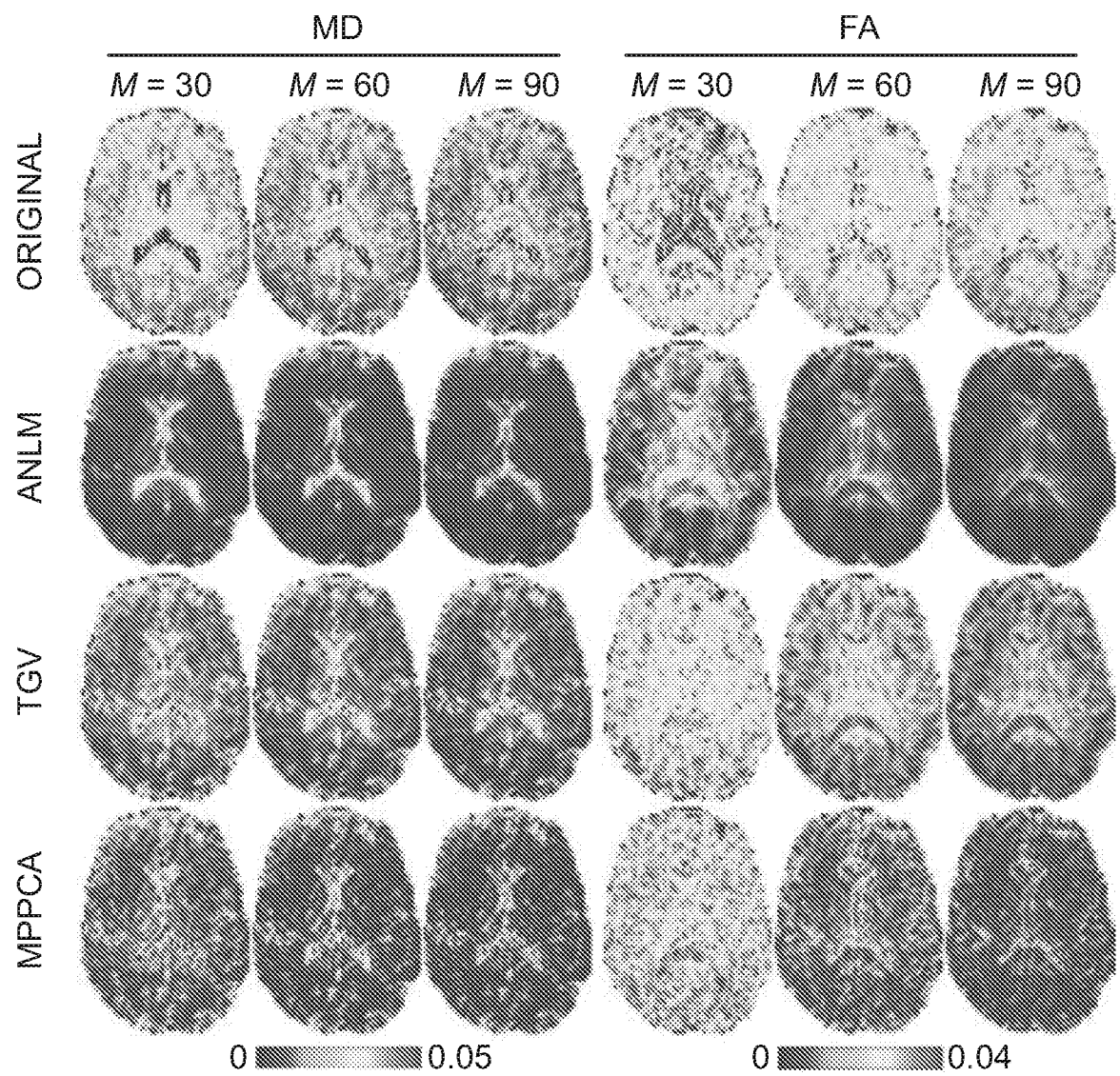
FIG. 15 is a set of maps illustrating the effect of denoising according to an exemplary embodiment of the present disclosure.
Figure 16:
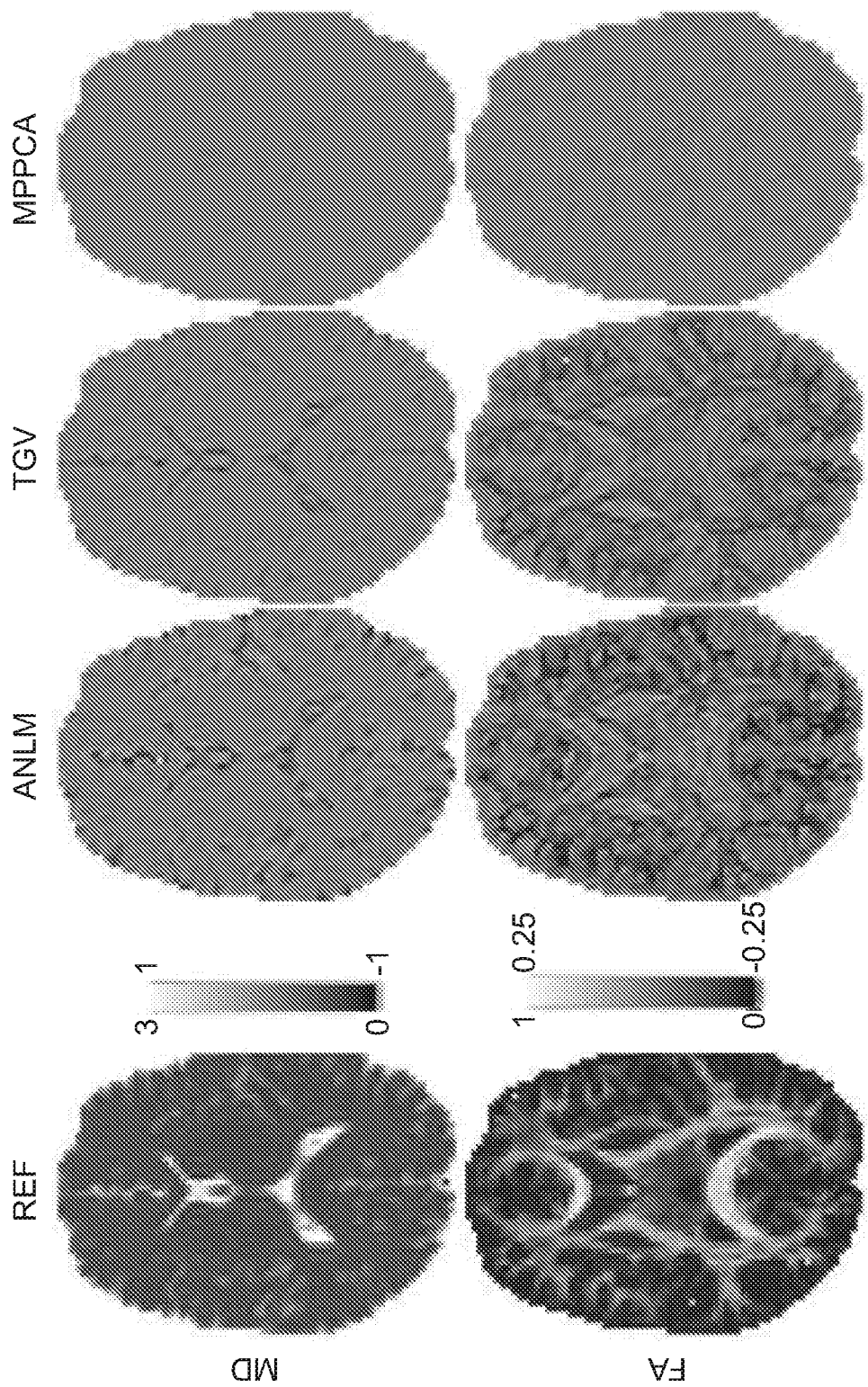
FIG. 16 is a further set of maps illustrating the effect of denoising according to an exemplary embodiment of the present disclosure.

The apparent blurring for ANLM and TGV (e.g., elements 1305 and 1310 of FIG. 13) can be quantitatively confirmed by comparing the k-energy density (see, e.g., Reference 29) (integrated over a narrow square shell in 2d), as function of the distance to the k-space center k. Given the exemplary discrete k-space grid $\hat{u}_k$, $[n_x \times n_y]$, with frequency resolution $\Delta k$, the k-energy density can be computed as $\|\hat{u}_k(\Omega(n_k \Delta k))\|_2$ for $n_k$=1 to min $(n_x, n_y)$ with $\Omega(n \Delta k)$ being the 2d square shell centered around the k-space center. A reference energy density can be predicted by subtracting the noise power $N_\Omega \sigma^2$ with $N_\Omega$ the number of samples in $\Omega$ from the corresponding k-space density of the original data (e.g., element 1315 of FIG. 13). This normalized quantity shows the observed loss of higher frequencies for ANLM and TV (e.g., low-pass filtering). Spatial resolution loss and blur can be the direct consequence. The suppression of frequencies that may not be strictly rooted in thermal noise can also result in residuals that can follow a distribution with standard deviation exceeding the noise standard deviation (e.g., meaning that they can be contaminated by signal). Thus, the exemplary MPPCA (e.g., element 1320 of FIG. 13) can preserve the actual signal better than competing methods (e.g., element 1325). In FIG. 14, denoised diffusion weighted images of the HCP data with b={0, 1, 3, 5, and 10} ms/µm² are shown. The data quality enhancement can be visible in all methods. However, significant differences can be noticeable. Overall, MPPCA preserves anatomical detail better than ANLM and TGV. Moreover, artifactual features present in TGV at high b may not be shown in MPPCA. The MPPCA residuals do not show anatomical details. Indeed, only a spatially varying noise trend can be observed, and this can be in line with previous results as a marker for accuracy. Bootstrapping (n=500) with replacement based on the 3 repetitions was used to assess the effect of the different denoising strategies on the variability in FA and MD maps. (See, e.g., FIG. 15). Note that the gradient directions for every single generated data set were the same. All denoising procedures improve the precision of diffusion parameter estimators, in all structures of the brain. The excelling results of ANLM in terms of precision can be superficial. It can look as if ANLM does a good job, however studying the residuals between the denoised results and a ground truth from 3×[5×b=0] and 3×[90×b=1 ms/μm²] (M=15+270), severe biases are revealed. Indeed, by averaging the residual maps between parameters maps with and without denoising, the systematic differences for ANLM and TGV in every brain structure can be seen. (See, e.g., FIG. 16). The differences root in the accumulation of signal inaccuracies introduced during denoising of the individual images. The exemplary MPPCA shows structure-free, zero-centered residuals for MD and FA.

Figure 17:
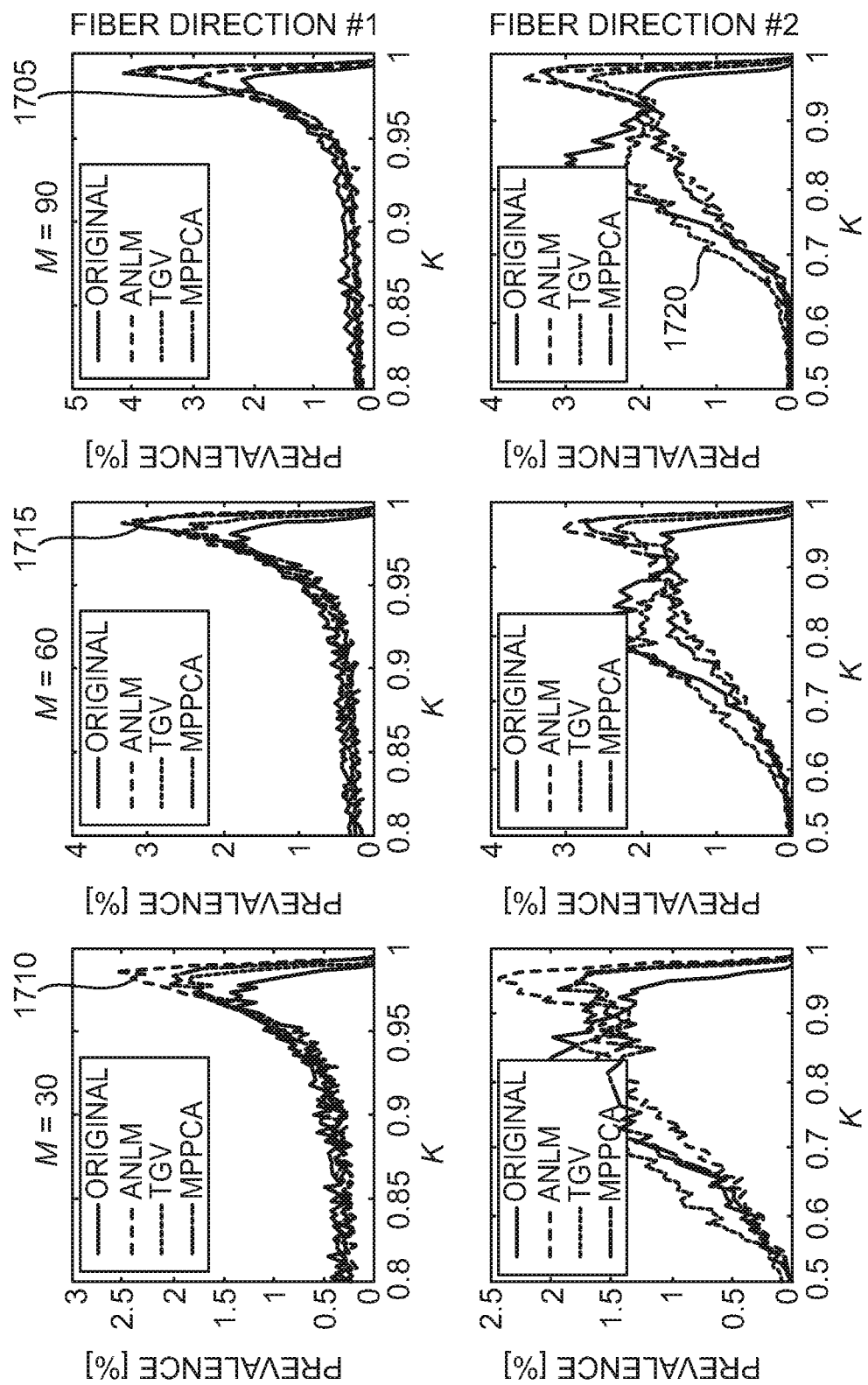
FIG. 17 is a set of graphs illustrating the effect of denoising on the angular precision according to an exemplary embodiment of the present disclosure.
Figure 17:
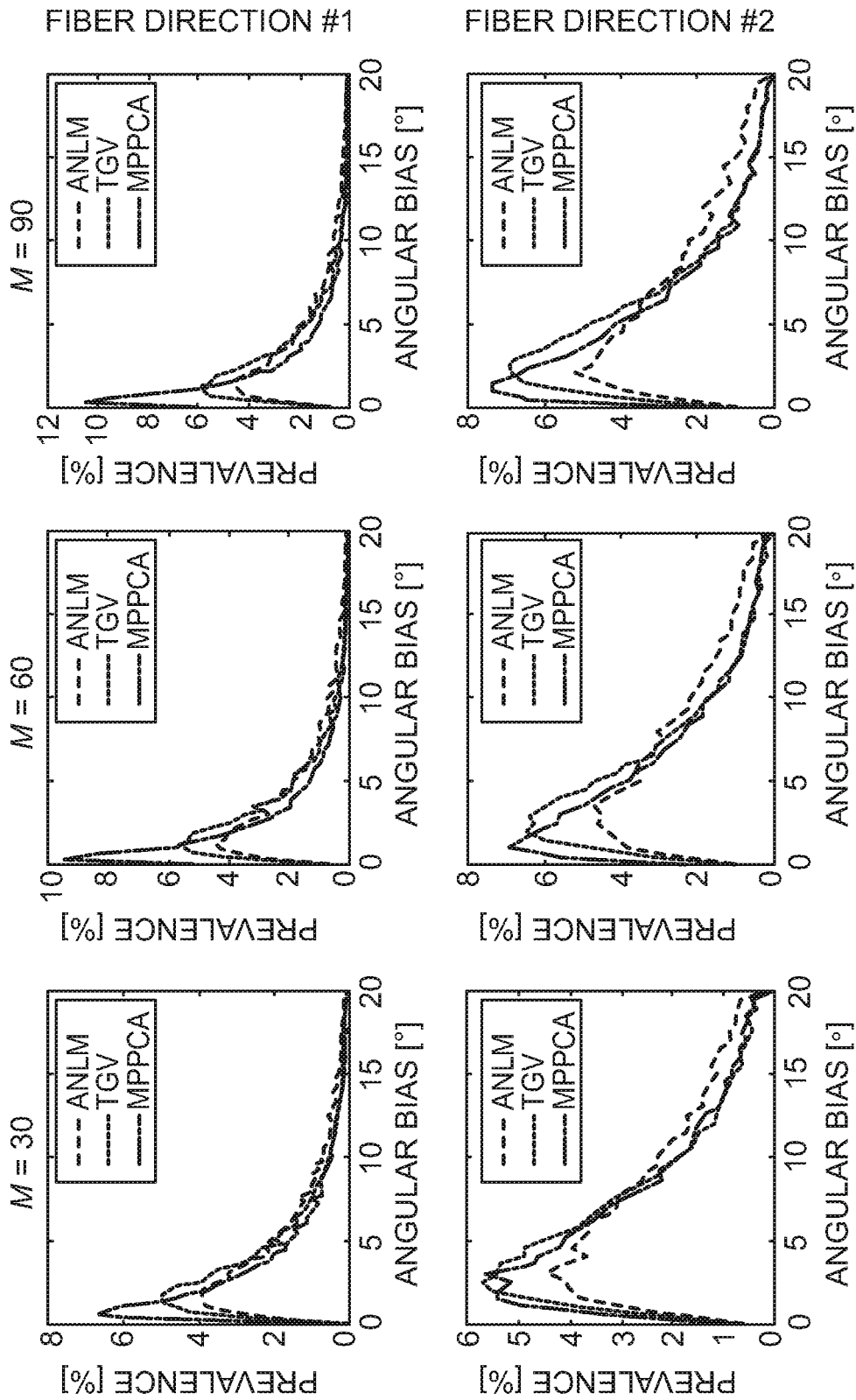
Figure 18:
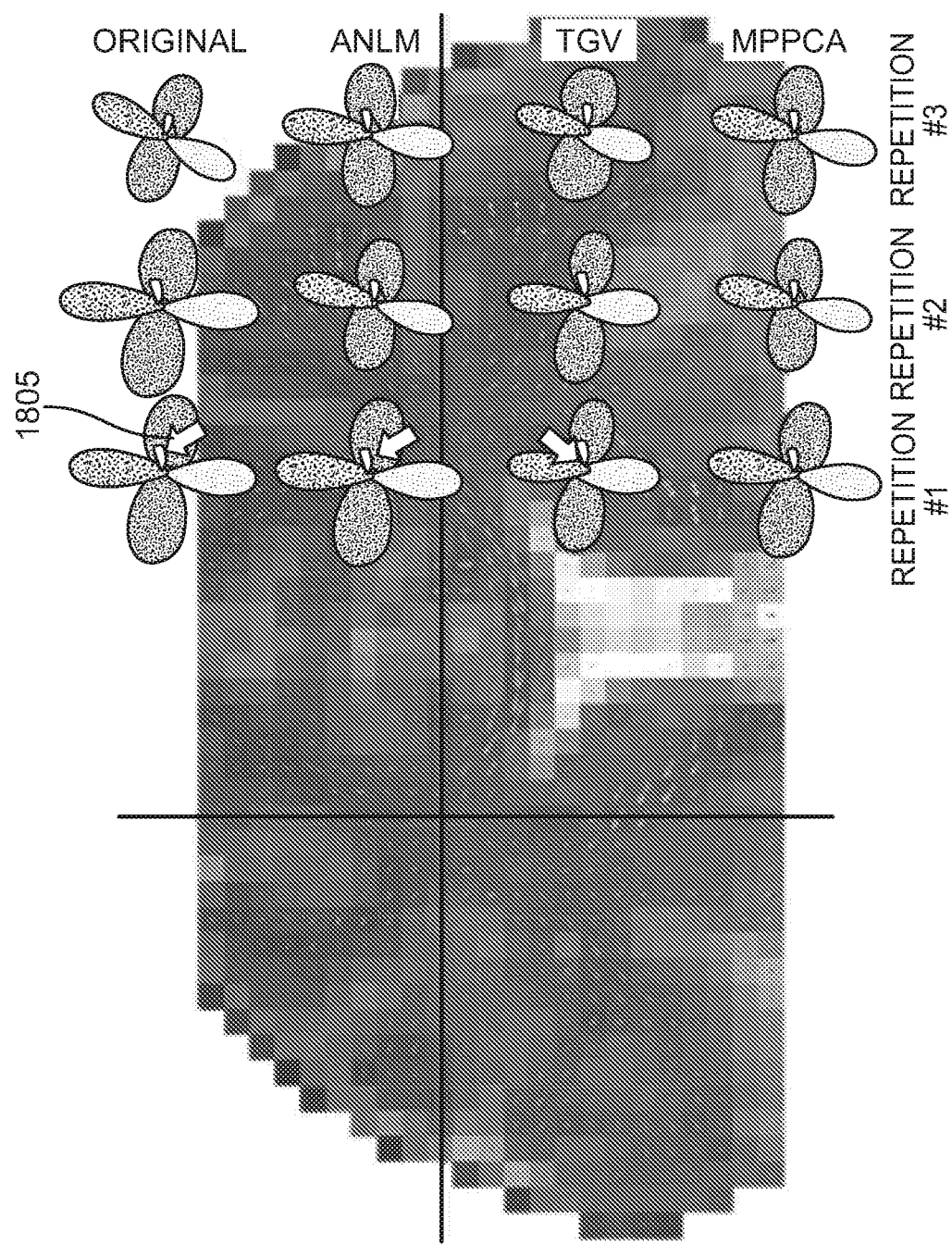
FIG. 18 is an image illustrating effect of denoising on the fiber orientation distribution function for a voxel with a three-fiber crossing according to an exemplary embodiment of the present disclosure.

A similar bootstrapping approach can be used to evaluate the effect on the estimation of diffusion directions using constrained spherical convolution. The distribution of angular precision, probed by the coherence metric κ (Eq. [12]), and the angular deviation from original (e.g., element 1705) data amongst white matter voxels is shown in the graphs FIG. 17. Again, for all evaluated M, ANLM (e.g., element 1710), MPPCA (e.g., element 1715) and—to a lesser degree—TGV (e.g., element 1720) improve the variability or dispersion in the primary and secondary diffusion directions. However, consistent with previous results, MPPCA can outperform all other methods in terms of accuracy. MPPCA shows minimal angular deviation from the original data, whereas the deviations can be significantly higher for TGV, and more so for ANLM. In the image of FIG. 18, the fODF corresponding to a single voxel is shown for each of the three repetitions (limited to $M_{b=2.5}=60$), with and without applying the different denoising techniques. In the particular voxel, the callosal commissure, superior longitudinal fasciculus and corticospinal tract cross. This complex fiber crossing can be assumed to be represented by a fODF with three distinct lobes. The success rate to detect the third lobe can depend on the method used. MPPCA returns in about 98% of the n=500 bootstrap realizations exactly three distinct peaks. The success rate lowers to about 65% and about 48% for ANLM and TGV, respectively, whereas no denoising results in a success rate of about 70%. A spurious fourth peak (around 1805 in FIG. 18) can be detected in about 2%, about 30%, about 52% and about 28% of the cases for MPPCA, ANLM, TGV and original, respectively. Additionally, a probabilistic tractography was performed on the denoised images corresponding to one of the repetitions (again restricted to $M_{b=2.5}=60$) to render digital reconstructions of the major fiber pathways as colorful tubes (See, e.g., original data, 1905, ANLM 1920, 1915 and MPPCA 1920 in the image of FIG. 19). (See, e.g., Reference 52). Some obvious spurious fibers aside, all tractograms look perfectly plausible, yet very different, especially towards the cortical areas. Those differences reflect the differences in noise and signal patterns that depend on the used denoising technique. (See e.g., FIGS. 10-13, 17 and 18).

Exemplary Conclusion

Promising results were obtained in suppressing the Gibbs artifact by extrapolation k-space data beyond the measurements by means of second order TGV minimization. The second order TGV framework inherently assumes that the underlying MR data can be modeled by a piecewise linear function. However, since the extrapolation of the k-space can be solely based on that model assumption, fine anatomical details that can be concealed in the unmeasured part of the k-space might not be recovered. Full recovery would need at least a random sampling of the k-space, including the high frequencies (e.g., compared to Compressed Sensing theory). Nonetheless, it was shown signal model parameters can be estimated more robustly and accurately, for example, without violating physical constraints, using the TGV-based Gibbs ringing correction. Moreover, unlike filtering techniques, the exemplary system, method and computer-accessible medium can affect the actually measured k-space data ($k<k_c$) and, as such, can maintain the acquisition resolution.

The exemplary system, method and computer-accessible medium can couple the local PCA/singular value decomposition ("SVD") with the RMT results such as the one due to Marchenko and Pastur, in order to distinguish between the noise and signal components in a model-independent way, and without the need of an empirically set threshold value on eigenvalues of the principal components. (See, e.g., Reference 13). The exemplary RMT-PCA procedure outperforms known spatially varying noise estimation methods, and does not need acquisition of repeated measurements, instead utilizing data redundancy. The results easily generalize onto a non-Gaussian MR distribution (see, e.g., Reference 9), and can be applied in all redundant time series, such as diffusion-weighted MR, T2/T2*, functional MR, or dynamic contrast-enhanced/dynamic susceptibility contrast MRI.

The exemplary system, method and computer-accessible medium can couple the local PCA/singular value decomposition ("SVD") with the RMT results such as the one due to Marchenko and Pastur, in order to distinguish between the noise and signal components in a model-independent way, and without the need of an empirically set threshold value on eigenvalues of the principal components. (See, e.g., Reference 13). The noise components can be nullified as a result of which noise can be removed in the resulting data. The exemplary MPPCA procedure outperforms known denoising techniques in terms of accuracy as it has been shown to preserve the signal better than competing methods. The results easily generalize onto a non-Gaussian MR distribution (see, e.g., Reference 9), and can be applied in all redundant time series, such as diffusion-weighted MR, T2/T2*, functional MR, or dynamic contrast-enhanced/dynamic susceptibility contrast MRI.

Figure 20A:
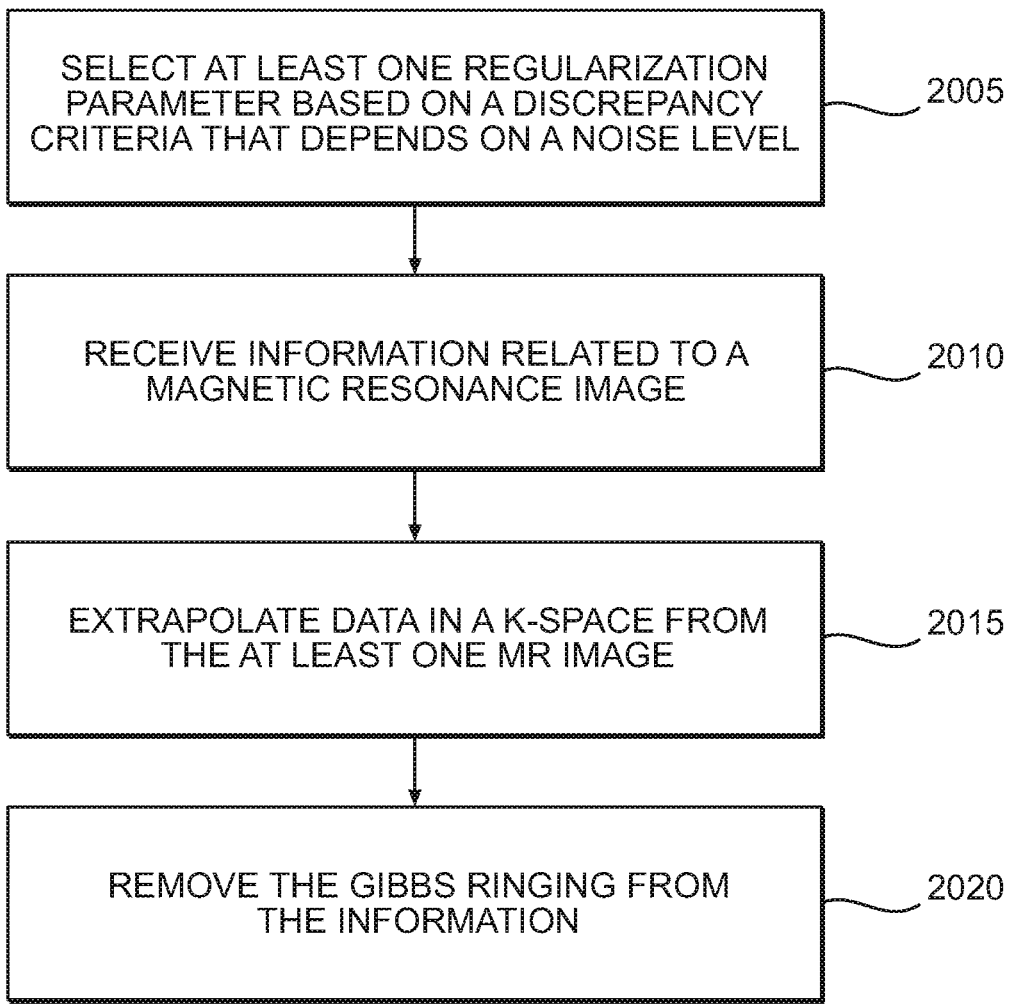
FIG. 20A is an exemplary flow diagram of an exemplary method for removing Gibbs ringing from a magnetic resonance image according to an exemplary embodiment of the present disclosure.

FIG. 20A is an exemplary flow diagram of an exemplary method 2000 for removing Gibbs ringing from a magnetic resonance image according to an exemplary embodiment of the present disclosure. For example, at procedure 2005 at least one regularization parameter can be selected based on at least one discrepancy criteria that can depend on the noise level. At procedure 2010, information related to a at least one MR image can be received. At procedure 2015, data in a k-space can be extrapolated from the at least one MR image beyond at least one edge of a measured portion of the k-space. At procedure 2020, the Gibbs ringing can be removed from the information.

Figure 20B:
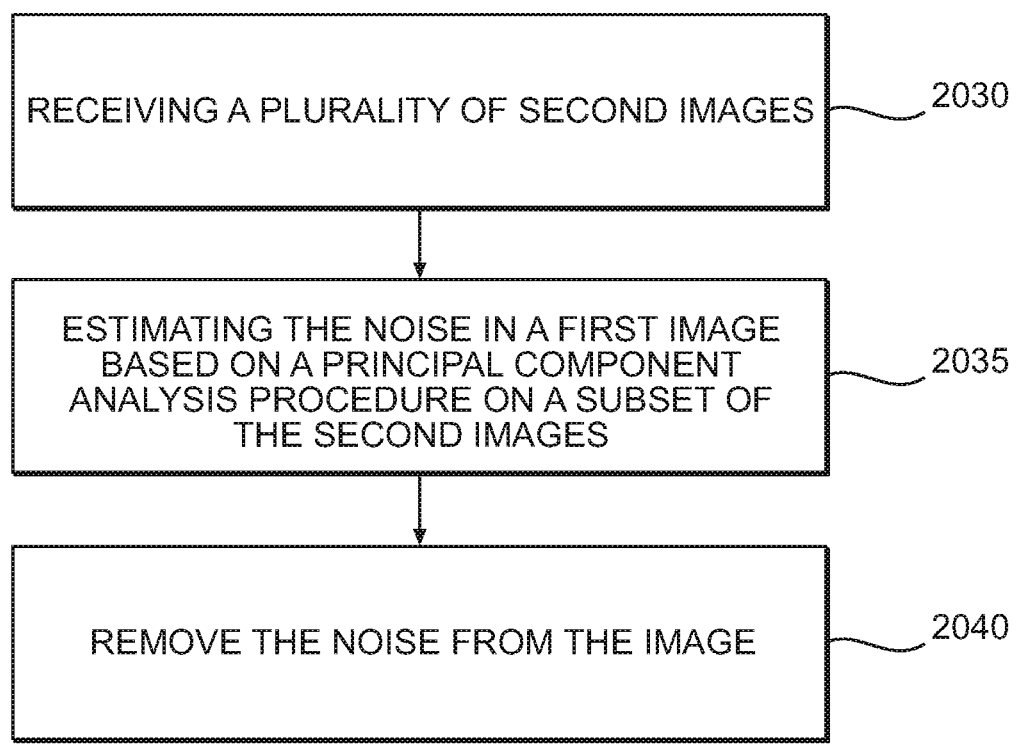
FIG. 20B is an exemplary flow diagram of an exemplary method for estimating a noise in a first image according to an exemplary embodiment of the present disclosure.

FIG. 20B is an exemplary flow diagram of an exemplary method 2025 for estimating a noise in a first image according to an exemplary embodiment of the present disclosure. For example at procedure 2030, a plurality of second images can be received. At procedure 2035, the noise in the at least one first image can be estimated based on a principal component analysis procedure on a subset of the second images. At procedure 2040, the noise can be removed from the at least one first image.

Figure 20C:
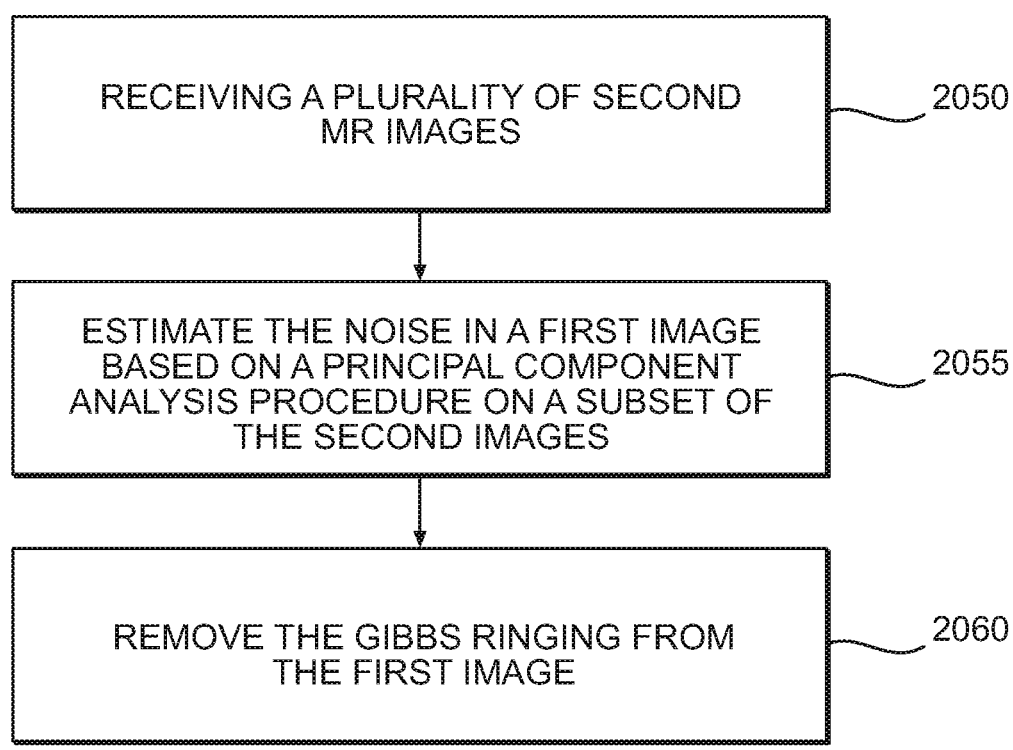
FIG. 20C is an exemplary flow diagram of an exemplary method for removing Gibbs ringing from a first magnetic resonance image according to an exemplary embodiment of the present disclosure.
Figure 21:
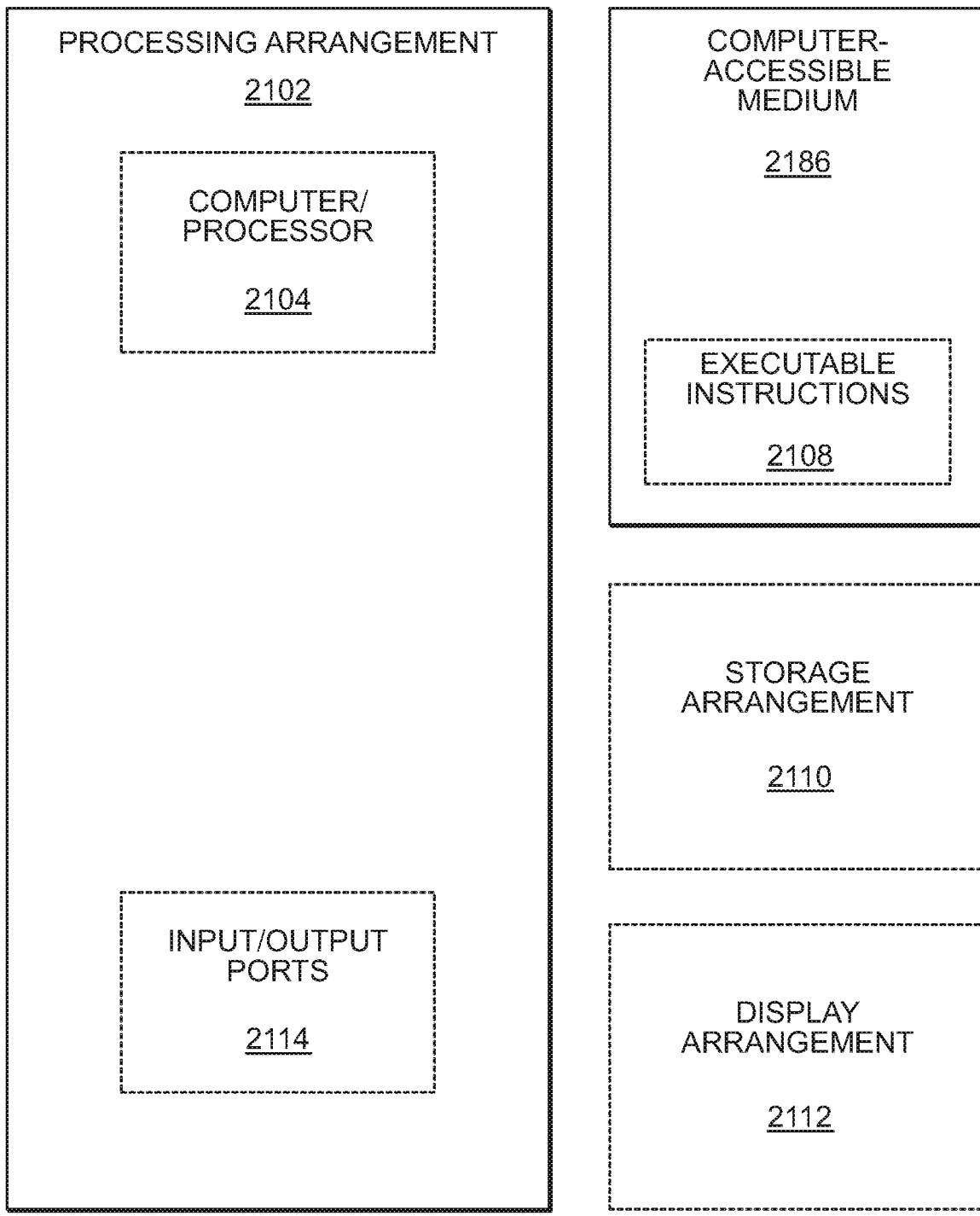
FIG. 21 is an illustration of an exemplary block diagram of an exemplary system in accordance with certain exemplary embodiments of the present disclosure.

FIG. 20C is an exemplary flow diagram of an exemplary method 2045 for removing Gibbs ringing from a first magnetic resonance image according to an exemplary embodiment of the present disclosure. For example, at procedure 2050, a plurality of second magnetic resonance images can be received. At procedure 2055, the noise in the at least one first magnetic resonance image can be estimated based on a principal component analysis ("PCA") procedure on a subset of the second magnetic resonance images. At procedure 2060, the Gibbs ringing can be removed from the at least one first magnetic resonance image by extrapolating data in a k-space, based on the noise, from the at least one first magnetic resonance image beyond at least one edge of a measured portion of the k-space FIG. 21 shows a block diagram of an exemplary embodiment of a system according to the present disclosure. For example, exemplary procedures in accordance with the present disclosure described herein can be performed by a processing arrangement and/or a computing arrangement 2102. Such processing/computing arrangement 2102 can be, for example entirely or a part of, or include, but not limited to, a computer/processor 2104 that can include, for example one or more microprocessors, and use instructions stored on a computer-accessible medium (e.g., RAM, ROM, hard drive, or other storage device).

As shown in FIG. 21, for example a computer-accessible medium 2106 (e.g., as described herein above, a storage device such as a hard disk, floppy disk, memory stick, CD-ROM, RAM, ROM, etc., or a collection thereof) can be provided (e.g., in communication with the processing arrangement 2102). The computer-accessible medium 2106 can contain executable instructions 2108 thereon. In addition or alternatively, a storage arrangement 2110 can be provided separately from the computer-accessible medium 2106, which can provide the instructions to the processing arrangement 2102 so as to configure the processing arrangement to execute certain exemplary procedures, processes and methods, as described herein above, for example.

Further, the exemplary processing arrangement 2102 can be provided with or include an input/output arrangement 2114, which can include, for example a wired network, a wireless network, the internet, an intranet, a data collection probe, a sensor, etc. As shown in FIG. 21, the exemplary processing arrangement 2102 can be in communication with an exemplary display arrangement 2112, which, according to certain exemplary embodiments of the present disclosure, can be a touch-screen configured for inputting information to the processing arrangement in addition to outputting information from the processing arrangement, for example. Further, the exemplary display 2112 and/or a storage arrangement 2110 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

1. Knoll et al. MRM 65:480(2011)
2. Block et al. Int. J. of Biomed. Imag.: ID 184123 (2008)
3. Perrone et al. 4th ISMRM Benelux Chapter, p. 99 (2012)
4. Hunt IEEE Trans Comput 22:805(1973)
5. Bredies et al. SIAM J Imaging Sci 3:492 (2010)
6. Chambolle et al. of Math Imag and Vision 40:120(2010)
7. Fieremans et al. NeuroImage 58:177 (2011)
8. Marchenko et al. (1967) Mat. Sb. (N.S.), 72(114), 507-536
9. Koay et al. (2006) JMR 179(2):317-22
10. Coupé et al. (2010) MEDIA, 14(4), 483-93
11. Veraart et al. (2013) MRM 70(4), 972-84
12. Maximov et al. (2012) Med Imag Anal 16:536-548
13. Mangon et al. (2013) Plos One, DOI: 10.1371/journal.pone.0073021
14. Jones D K. Diffusion MRI: Theory, methods, and applications. Oxford University Press, 2010.
15. Jones D K. Precision and accuracy in diffusion tensor magnetic resonance imaging. Topics in Magnetic Resonance Imaging 2010; 21:87-99.
16. Jones D, Horsfield M, Simmons A. Optimal strategies for measuring diffusion in anisotropic systems by magnetic resonance imaging. Magnetic Resonance in Medicine 1999; 42.
17. Poot D H J, den Dekker A J, Achten E, Verhoye M, Sijbers J. Optimal experimental design for diffusion kurtosis imaging. Medical Imaging, IEEE Transactions on 2010; 29:819-829.
18. Buades A, Coll B, Morel J M. A non-local algorithm for image de-noising. In: Computer Vision and Pattern Recognition. IEEE Computer Society Conference on. IEEE, volume 2, 2005; 60-65.
19. Coupé P, Yger P, Barillot C. Fast non local means denoising for 3D MR images. In: Medical Image Computing and Computer-Assisted Intervention-MICCAI 2006, Springer. 2006; 33-40.
20. Manjón J V, Carbonell-Caballero J, Lull J J, Garc'a-Mart' G, Mart'-Bonmat' L, Robles M. MRI denoising using non-local means. Medical image analysis 2008; 12:514-523.
21. Manjón J V, Coupé P, Mart'-Bonmat' L, Collins D L, Robles M. Adaptive non-local means denoising of MR images with spatially varying noise levels. Journal of Magnetic Resonance Imaging 2010; 31:192-203.
22. Orchard J, Ebrahimi M, Wong A. Efficient nonlocal-means denoising using the SVD. In: Image Processing, 2008. ICIP 2008. 15th IEEE International Conference on. IEEE, 2008; 1732-1735.
23. Rajan J, Jeurissen B, Verhoye M, Van Audekerke J, Sijbers J. Maximum likelihood estimation-based denoising of magnetic resonance images using restricted local neighborhoods. Physics in Medicine and biology 2011; 56:5221.
24. Rajan J, Veraart J, Van Audekerke J, Verhoye M, Sijbers J. Nonlocal maximum likelihood estimation method for denoising multiple-coil magnetic resonance images. Magnetic Resonance imaging 2012; 30:1512-1518.
25. Foi A. Noise estimation and removal in mr imaging: The variance-stabilization approach. In: Biomedical Imaging: From Nano to Macro, 2011 IEEE International Symposium on. IEEE, 2011; 1809-1814.

26. Rudin L I, Osher S, Fatemi E. Nonlinear total variation based noise removal algorithms. Physica D: Nonlinear Phenomena 1992; 60:259-268.
27. Block K T, Uecker M, Frahm J. Suppression of MRI truncation artifacts using total variation constrained data extrapolation. International journal of biomedical imaging 2008.
28. Knoll F, Bredies K, Pock T, Stollberger R. Second order total generalized variation (TGV) for MRI. Magnetic Resonance in Medicine 2011; 65:480-491.
29. Veraart J, Fieremans E, Jelescu I O, Knoll F, Novikov D S. Gibbs ringing in diffusion MRI. Magnetic Resonance in Medicine 2015; DOI: 10.1002/mrm.25866.
30. Perrone D, Aelterman J, Pizurica A, Jeurissen B, Philips W, Lee-mans A. The effect of Gibbs ringing artifacts on measures derived from diffusion MRI. NeuroImage 2015; 120:441-455.
31. Hotelling H. Analysis of a complex of statistical variables into principal components. Journal of educational psychology 1933; 24:417.
32. Deledalle C A, Salmon J, Dalalyan A S, et al. Image denoising with patch based PCA: local versus global. In: BMVC. 2011; 1-10.
33. Manjón J V, Coupé P, Buades A. MRI noise estimation and denoising using non-local PCA. Medical image analysis 2015; 22:35-47.
34. Veraart J, Fieremans E, Novikov D S. Diffusion MRI noise mapping using random matrix theory. Magnetic Resonance in Medicine 2016; DOI: 10.1002/mrm.26059.
35. Manjón J V, Coupé P, Concha L, Buades A, Collins D L, Robles M. Diffusion weighted image denoising using overcomplete local PCA. PloS one 2013; 8:e73021.
36. Marchenko V A, Pastur L A. Distribution of eigenvalues for some sets of random matrices. Matematicheskii Sbornik 1967; 114:507-536.
37. Aja-Fernández S, Tristán-Vega A, Hoge W S. Statistical noise analysis in GRAPPA using a parametrized noncentral Chi approximation model. Magnetic Resonance in Medicine 2011; 65:1195-1206.
38. Gudbjartsson H, Patz S. The Rician distribution of noisy MRI data. Magnetic Resonance in Medicine 1995; 34:910-914.
39. Koay C G, Basser P J. Analytically exact correction scheme for signal extraction from noisy magnitude MR signals. Journal of Magnetic Resonance 2006; 179:317-322.
40. Johnstone I M. High dimensional statistical inference and random matrices. arXiv preprint math/0611589 2006.
41. Setsompop K, Kimmlingen R, Eberlein E, Witzel T, Cohen-Adad J, McNab J A, Keil B, Tisdall M D, Hoecht P, Dietz P, et al. Pushing the limits of in vivo diffusion MRI for the Human Connectome Project. Neuroimage 2013; 80:220-233.
42. Keil B, Blau J N, Biber S, Hoecht P, Tountcheva V, Setsompop K, Triantafyllou C, Wald L L. A 64-channel 3T array coil for accelerated brain MRI. Magnetic Resonance in Medicine 2013; 70:248-258.
43. Basser P J, Mattiello J, LeBihan D. MR diffusion tensor spectroscopy and imaging. Biophysical journal 1994; 66:259-267.
44. Veraart J, Sijbers J, Sunaert S, Leemans A, Jeurissen B. Weighted linear least squares estimation of diffusion MRI parameters: strengths, limitations, and pitfalls. NeuroImage 2013; 81:335-346.
45. Tournier J D, Calamante F, Connelly A. Robust determination of the fibre orientation distribution in diffusion MRI: non-negativity constrained super-resolved spherical deconvolution. NeuroImage 2007; 35:1459-1472.
46. Tax C M, Jeurissen B, Vos S B, Viergever M A, Leemans A. Recursive calibration of the fiber response function for spherical deconvolution of diffusion mri data. Neuroimage 2014; 86:67-80.
47. Jeurissen B, Leemans A, Tournier J D, Jones D K, Sijbers J. Investigating the prevalence of complex fiber configurations in white matter tissue with diffusion magnetic resonance imaging. Human brain mapping 2013; 34:2747-2766.
48. Glasser M F, Sotiropoulos S N, Wilson J A, Coalson T S, Fischl B, Andersson J L, Xu J, Jbabdi S, Webster M, Polimeni J R, et al. The minimal preprocessing pipelines for the Human Connectome Project. Neuroimage 2013; 80:105-124.
49. Efron B. Bootstrap methods: another look at the jackknife. Springer, 1992.
50. Jones D K. Determining and visualizing uncertainty in estimates of fiber orientation from diffusion tensor MRI. Magnetic Resonance in Medicine 2003; 49:7-12.
51. Basser P J, Pajevic S. Statistical artifacts in diffusion tensor MRI (DT-MRI) caused by background noise. Magnetic Resonance in Medicine 2000; 44:41-50.
52. Jeurissen B, Leemans A, Jones D K, Tournier J D, Sijbers J. Probabilistic fiber tracking using the residual bootstrap with constrained spherical deconvolution. Human brain mapping 2011; 32:461-479. 40. Johnson J B. Thermal agitation of electricity in conductors. Physical review 1928; 32:97.
53. Nyquist H. Thermal agitation of electric charge in conductors. Physical review 1928; 32:110.
54. Chang L C, Jones D K, Pierpaoli C. RESTORE: robust estimation of tensors by outlier rejection. Magnetic Resonance in Medicine 2005; 53:1088-1095.
55. Kellner E, Dhital B, Kiselev V G, Reisert M. Gibbs-ringing artifact removal based on local subvoxel-shifts. Magnetic Resonance in Medicine 2015; doi: 10.1002/mrm.26054.
56. Smith S M, Jenkinson M, Woolrich M W, Beckmann C F, Behrens T E, Johansen-Berg H, Bannister P R, De Luca M, Drobnjak I, Flitney D E, et al. Advances in functional and structural MR image analysis and implementation as FSL. Neuroimage 2004; 23:S208-S219.
57. Sotiropoulos S N, Jbabdi S, Xu J, et al. Advances in diffusion MRI acquisition and processing in the Human Connectome Project. Neuroimage 2013; 80:125-143.
58. Jones D K, Basser P J. "Squashing peanuts and smashing pumpkins": How noise distorts diffusion-weighted MR data. Magnetic Resonance in Medicine 2004; 52:979-993.
59. Veraart J, Rajan J, Peeters R R, Leemans A, Sunaert S, Sijbers J. Comprehensive framework for accurate diffusion MRI parameter estimation. Magnetic Resonance in Medicine 2013; 70:972-984.
60. Veraart J, Poot D H J, Van Hecke W, Blockx I, Van der Linden A, Verhoye M, Sijbers J. More accurate estimation of diffusion tensor parameters using diffusion kurtosis imaging. Magnetic Resonance in Medicine 2011; 65:138-145.
61. Veraart J, Van Hecke W, Sijbers J. Constrained maximum likelihood estimation of the diffusion kurtosis tensor using a Rician noise model. Magnetic Resonance in Medicine 2011; 66:678-686.
62. Laloux L, Cizeau P, Bouchaud J P, Potters M. Noise dressing of financial correlation matrices. Physical review letters 1999; 83:1467.

63. Ahmed A, Hu Y F, Noras J M. Noise variance estimation for spectrum sensing in cognitive radio networks. AASRI Procedia 2014; 9:37-43.
64. Ding Y, Chung Y C, Simonetti O P. A method to assess spatially variant noise in dynamic MR image series. Magnetic Resonance in Medicine 2010; 63:782-789.
65. Jahani J, Johnson G, Kiselev V G, Novikov D S. Random matrix theory-based noise reduction for dynamic imaging: Application to DCE-MRI. In: Proceedings 21th Scientific Meeting, International Society for Magnetic Resonance in Medicine. Salt Lake City, USA, 2013; 3073.
66. Sengupta A M, Mitra P P. Distributions of singular values for some random matrices. Physical Review E 1999; 60:3389.
67. Jelescu I O, Veraart J, Fieremans E, Novikov D S. Degeneracy in model parameter estimation for multi-compartmental diffusion in neuronal tissue. NMR in Biomedicine 2016; 29:33-47.

What is claimed is:

1. A non-transitory computer-accessible medium having stored thereon computer-executable instructions for estimating a noise in at least one first image, wherein, when a computer arrangement executes the instructions, the computer arrangement is configured to perform procedures comprising:
   receiving a plurality of second images; and
   estimating the noise in the at least one first image based on a principal component analysis ("PCA") procedure on a subset of the second images.

2. The computer-accessible medium of claim 1, wherein the computer arrangement estimates the noise level based on a set of eigenvalues resulting from the PCA procedure.

3. The computer-accessible medium of claim 2, wherein the computer arrangement estimates the noise level based on a noise-only distribution of a subset of the eigenvalues.

4. The computer-accessible medium of claim 3, wherein the noise-only distribution includes eigenvalues of a PCA Eigen spectrum that is described by a Marchenko-Pastur distribution.

5. The computer-accessible medium of claim 2, wherein the computer arrangement is further configured to remove the noise from the at least one first image using the set of eigenvalues.

6. The computer-accessible medium of claim 1, wherein the second images include, at least one of diffusion-weighted magnetic resonance images, or a set of images obtained from different cons or channels in a multichannel magnetic resonance imaging apparatus.

7. The computer-accessible medium of claim 1, wherein the computer arrangement is further configured to remove the noise from the at least one first image.

8. The computer-accessible medium of claim 7, wherein the computer arrangement is configured to identify a threshold between only the noise and at least one principal component of the PCA procedure.

9. The computer-accessible medium of claim 8, wherein the computer arrangement is configured to identify the threshold based on at least one noisy covariance matrix.

10. The computer-accessible medium of claim 9, wherein the computer arrangement is configured to remove the noise based on the threshold.

11. The computer-accessible medium of claim 10, wherein the computer arrangement is configured to remove the noise by removing at least one noise-only component of the at least one first image.

12. The computer-accessible medium of claim 7, wherein the computer arrangement is configured to remove the noise using at least one Marchenko-Pastur distribution.

13. A system for estimating a noise in at least one first image, comprising:
   a computer hardware arrangement configured to:
   receive a plurality of second images; and
   estimate the noise in the at least one first image based on a principal component analysis ("PCA") procedure on a subset of the second images.

14. A method for estimating a noise in at least one first image, comprising:
   receiving a plurality of second images; and
   using a computer hardware arrangement, estimating the noise in the at least one first image based on a principal component analysis ("PCA") procedure on a subset of the second images.

15. A non-transitory computer-accessible medium having stored thereon computer-executable instructions for removing Gibbs ringing from at least one first magnetic resonance (MR) image, wherein, when a computer arrangement executes the instructions, the computer arrangement is configured to perform procedures comprising:
   receiving a plurality of second MR images;
   estimating the noise in the at least one first image based on a principal component analysis ("PCA") procedure performed on a subset of the second images; and
   removing the Gibbs ringing from the at least one first MR image by extrapolating data in a k-space, based on the noise, from the at least one first MR image beyond at least one edge of a measured portion of the k-space.

* * * * *

UNITED STATES PATENT AND TRADEMARK OFFICE
CERTIFICATE OF CORRECTION

PATENT NO. : 10,698,065 B2
APPLICATION NO. : 15/574467
DATED : June 30, 2020
INVENTOR(S) : Dmitry Novikov, Jelle Veraart and Els Fieremans It is certified that error appears in the above-identified patent and that said Letters Patent is hereby corrected as shown below:

In the Specification

Please add a paragraph to include a Statement Regarding Federally Sponsored Research, under Column 1, after the "Cross-Reference to Related Application(s)" section, starting on Line 16, with the following paragraph:

"STATEMENT REGARDING FEDERALLY SPONSORED RESEARCH
This invention was made with government support under grant number R01 NS088040 awarded by The National Institutes of Health. Therefore, the government has certain rights in the invention."

Signed and Sealed this
Seventeenth Day of January, 2023

Katherine Kelly Vidal
*Director of the United States Patent and Trademark Office*